US006797274B1

(12) United States Patent
Ruelle

(10) Patent No.: US 6,797,274 B1
(45) Date of Patent: Sep. 28, 2004

(54) COMPOUNDS

(75) Inventor: Jean-Louis Ruelle, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 09/889,746

(22) PCT Filed: Jan. 19, 2000

(86) PCT No.: PCT/EP00/00428

§ 371 (c)(1),
(2), (4) Date: Dec. 31, 2001

(87) PCT Pub. No.: WO00/43519

PCT Pub. Date: Jul. 27, 2000

(30) Foreign Application Priority Data

| Jan. 22, 1999 | (GB) | ............................................. 9901368 |
| Jan. 28, 1999 | (GB) | ............................................. 9901944 |
| Jan. 29, 1999 | (GB) | ............................................. 9902086 |
| Feb. 15, 1999 | (GB) | ............................................. 9903417 |
| Feb. 16, 1999 | (GB) | ............................................. 9903535 |

(51) Int. Cl.[7] ...................... A61K 39/095; A61K 39/00; C07H 21/04; C07K 1/00
(52) U.S. Cl. ............................... 424/250.1; 424/249.1; 424/190.1; 424/185.1; 424/184.1; 530/300; 530/350; 536/23.1; 536/23.7; 536/24.1; 536/24.32; 435/69.1; 435/69.3; 435/24.3; 435/252.3
(58) Field of Search .......................... 424/154.1, 155.1, 424/190.1, 249.1, 250.1; 530/300, 350; 536/23.1, 23.7, 26.1, 26.32; 435/69.1, 69.3, 243, 252.3

(56) References Cited

FOREIGN PATENT DOCUMENTS

WO    WO9802547    1/1998

OTHER PUBLICATIONS

Rudinger et al, in "Peptide Hormones", edited by Parsons, J.A. University Park Press, Jun. 1976, p. 6.*
Burgess et al., The Journal of Cell Biology, 111:2129–2138, 1990.*
Lazar et al., Molecular and Cellular Biology, 8(3): 1247–1252, 1988).*
Jobling et al. (Mol. Microbiol. 1991, 5(7): 1755–67 t.*
Ellis, R.W. (Chapter 29 of "Vaccines" Plotkin, 5.A. et al. (eds) published by W.B. Saunders company (Philadelphia) in 1988, Biotecnologia Aplicada 1996, vol. 13, 1–7.
Marin et al 1997 (J.Ex.Med. Vol. 185, No. 7, Apr. 7, 1997 1173–1184).
Martin D et al: "Highly Conserved Neisseria Meningitidis Surface Protein Confers Protection Against Experimental Infection" Journal of Experimental Medicine, vol. 185, No. 7.
Lissolo L et al: "Evaluation of Transferrin–Binding Protein 2 Within . . . " Infection and Immunity, vol. 63, No. 4, Mar. 1995, pp. 884–890.
Sato Y et al: "Immunostimulatory DNA Sequences Necessary for Effective Intradermal Gene Immunization" Science, vol. 273, Jul. 19, 1996 pp. 352–354.
Chee M et al: "Accessing Genetic Information with High–Density DNA Arrays" Science, vol. 274, Oct. 25, 1996 pp. 610–614.
Infection and Immunity 32, (1981) 592–599.
Infection and Immunity 62, (1991) 3017–3021.
Infection and Immunity 56, (1998) 977–983.
International Search Report for PCT/EP00/00428 (Dec. 7, 2000).
International Preliminary Examination Report for PCT/EP00/00428 (Jan. 15, 2001).

* cited by examiner

*Primary Examiner*—Lynette R. F. Smith
*Assistant Examiner*—Padma Baskar
(74) *Attorney, Agent, or Firm*—Jeffrey A. Sutton; Eric A. Meade

(57) ABSTRACT

The invention provides BASB047, BASB054, BASB068 and BASB069 polypeptides, and polynucleotides encoding BASBO47, BASB054, BASB068 and BASB069 polypeptides and methods for producing such polypeptides by recombinant techniques. Also provided are diagnostic, prophylactic and therapeutic uses.

10 Claims, No Drawings

SEQUENCE LISTING

<160> NUMBER OF SEQ ID NOS: 8

<210> SEQ ID NO 1
<211> LENGTH: 1203
<212> TYPE: DNA
<213> ORGANISM: Neisseria meningitidis

<400> SEQUENCE: 1

```
atgcgtcatt cccactattt tcaatggtta tctttgcctt tactaagtgt ggcagtaact      60
cagcagttgt acgctcaacc caatgagtca ttaccaacgg ttgaattaga gcctgtggtt     120
attaccattg ataagagcgg tatggcactt gccaatcgta tcacgcaaat gccccatacc     180
accaaagtta tttatgaaga gcaaattcaa gagcaagcaa caggctctcg acagcttgcc     240
gatgtgatgg cacagctcat tccaagtttg ggggtaagta gtggcactac cagtaacttt     300
gggcaaacca tgcacggtcg tcaagtgcaa ttttttgttaa atggcgtgcc tttgacaggt     360
tcgcgagaca tctctagaca gcttaatagt atcaatccca atcaagtggc tagaattgaa     420
gttttatcag gagcaaccag tatttatggg tctggagcaa caggcggttt gattaatatc     480
gttactaagt ctgatttgga agaggagcaa tttgaaaccc gcatcggtgt acatggtagt     540
aaattatcca gtgaaggtat cggttatcag gtaggtcaga gtgtagcagg tgtcagcgaa     600
aatggtaatg tccttgcacg acttgatgtc gactatcgca ccacaggagg ggcatttgat     660
gctaacggta aacgcatcgc tcctgagcct gcccaaactg ataagcaaga cagcaaaagc     720
ctaagtgtca atacaaatgt tgattggcaa cttgacgaca agcaaaatat caatctggca     780
ttgacgcatt ataacgacaa acaagatacc gattatgcac ctgattatgg taatcgcctt     840
gcggtgttgt ttggagaaaa gccttcatta aatgccatca aaggcttatc attatcagaa     900
cagccaaaaa ccaccaaaag cacctttaat atcaactatc atcatgatga tttgtggggt     960
aacaccatca ataccaatgc ttattatcgc agagagaaag gcagatttta tccctttgtt    1020
gccccgtttt cgatcgccaa agccctgcct attttacaaa gcatgaattt gccatcagcc    1080
actttggatg cttataccaa ggctccacaa gctcgcgcct atggggtgtt acaatccgaa    1140
tctaaggcag aggtactagg gcgtgtccct aatttgaata gcccaaaag agccctattt    1200 taa                                                                  1203
```

<210> SEQ ID NO 2
<211> LENGTH: 400
<212> TYPE: PRT
<213> ORGANISM: Neisseria meningitidis -continued

<400> SEQUENCE: 2

```
Met Arg His Ser His Tyr Phe Gln Trp Leu Ser Leu Pro Leu Leu Ser
 1               5                  10                  15
Val Ala Val Thr Gln Leu Tyr Ala Gln Pro Asn Glu Ser Leu Pro
            20                  25                  30
Thr Val Glu Leu Glu Pro Val Val Ile Thr Ile Asp Lys Ser Gly Met
            35                  40                  45
Ala Leu Ala Asn Arg Ile Thr Gln Met Pro His Thr Thr Lys Val Ile
    50                  55                  60
Tyr Glu Glu Gln Ile Gln Glu Gln Ala Thr Gly Ser Arg Gln Leu Ala
65                  70                  75                  80
Asp Val Met Ala Gln Leu Ile Pro Ser Leu Gly Val Ser Ser Gly Thr
                85                  90                  95
Thr Ser Asn Phe Gly Gln Thr Met His Gly Arg Gln Val Gln Phe Leu
            100                 105                 110
Leu Asn Gly Val Pro Leu Thr Gly Ser Arg Asp Ile Ser Arg Gln Leu
        115                 120                 125
Asn Ser Ile Asn Pro Asn Gln Val Ala Arg Ile Glu Val Leu Ser Gly
    130                 135                 140
Ala Thr Ser Ile Tyr Gly Ser Gly Ala Thr Gly Gly Leu Ile Asn Ile
145                 150                 155                 160
Val Thr Lys Ser Asp Leu Glu Glu Glu Gln Phe Glu Thr Arg Ile Gly
                165                 170                 175
Val His Gly Ser Lys Leu Ser Ser Glu Gly Ile Gly Tyr Gln Val Gly
            180                 185                 190
Gln Ser Val Ala Gly Val Ser Glu Asn Gly Asn Val Leu Ala Arg Leu
        195                 200                 205
Asp Val Asp Tyr Arg Thr Thr Gly Gly Ala Phe Asp Ala Asn Gly Lys
    210                 215                 220
Arg Ile Ala Pro Glu Pro Ala Gln Thr Asp Lys Gln Asp Ser Lys Ser
225                 230                 235                 240
Leu Ser Val Asn Thr Asn Val Asp Trp Gln Leu Asp Asp Lys Gln Asn
                245                 250                 255
Ile Asn Leu Ala Leu Thr His Tyr Asn Asp Lys Gln Asp Thr Asp Tyr
            260                 265                 270
Ala Pro Asp Tyr Gly Asn Arg Leu Ala Val Leu Phe Gly Glu Lys Pro
        275                 280                 285
Ser Leu Asn Ala Ile Lys Gly Leu Ser Leu Ser Glu Gln Pro Lys Thr
    290                 295                 300
Thr Lys Ser Thr Phe Asn Ile Asn Tyr His His Asp Asp Leu Trp Gly
305                 310                 315                 320
Asn Thr Ile Asn Thr Asn Ala Tyr Tyr Arg Arg Glu Lys Gly Arg Phe
                325                 330                 335
Tyr Pro Phe Val Ala Pro Phe Ser Ile Ala Lys Ala Leu Pro Ile Leu
            340                 345                 350
Gln Ser Met Asn Leu Pro Ser Ala Thr Leu Asp Ala Tyr Thr Lys Ala
        355                 360                 365
Pro Gln Ala Arg Ala Tyr Gly Val Leu Gln Ser Glu Ser Lys Ala Glu
    370                 375                 380
Val Leu Gly Arg Val Pro Asn Leu Asn Lys Pro Lys Arg Ala Leu Phe
385                 390                 395                 400
```

<210> SEQ ID NO 3

<211> LENGTH: 2409
<212> TYPE: DNA
<213> ORGANISM: Neisseria meningitidis

<400> SEQUENCE: 3

```
ttggctcgtt tattttcact caaaccactg gtgctggcat tgggcttctg cttcggcacg      60
cattgcgccg ccgccgatgc cgttgcggcg gaggaaacgg acaatccgac cgccggagga     120
agtgttcgga gcgtgtccga acccatgcag cctgccggcc tgagcctcgg ttcgacctgc     180
ctgttttgca gtaacgaaag cggcaaaccc gaaaaaaccg aatctgccgt caaaggaagc     240
ggcgaagggc ctgtgcccga aaccacacg cgaattgtcg ccgacaaggt ggaagggcag      300
tcgcaggtca aggtacgcgc ggagggcggc gtcgttgtcg aacgcaaccg gacgacccctt    360
aatgccgact gggcggatta cgaccagtcg ggcgacaccg ttaccgtagg cgaccggttc     420
gccctccaac aggacggtac gctgattcgg ggcgaaaccc tgacctacaa tctcgagcag     480
cagaccggcg aagcgcacaa cgtccgcatg gaaaccgaac aaggcggacg gcggctgcaa     540
agcgtcagcc gcaccgccga aatgttgggc gaagggcatt acaaactgac ggaaacccaa     600
ttcaacacct gttccgccgg cgatgccggc tggtatgtca aggcagcctc tgtcgaagcc     660
gatcgggaaa aaggcatagg cgttgccaaa cacgccgcct tcgtgttcgg cggcgttcct     720
attttctaca ccccttgggc ggacttcccg cttgacggca accgcaaaag cggcctgctt     780
gttccctcac tgtccgccgg ttcggacggc gtttcccttt ccgttcccta ttatttcaac     840
cttgccccca atctcgatgc cacgttcgcg cccagcgtga tcggcgaacg cggcgcggtc     900
tttgacgggc aggtacgcta cctgcggccg gattatgccg gccagtccga cctgacctgg     960
ctgccgcacg acaagaaaag cggcaggaat aaccgctatc aggcgaaatg gcagcatcgg    1020
cacgacattt ccgacacgct tcaggcgggt gtcgatttca ccaagtctc cgacagcggc     1080
tactaccgcg acttttacgg caacaaagaa atcgccggca acgtcaacct caaccgccgt    1140
gtatggctgg attatggcgg cagggcggcg ggcggcagcc tgaatgccgg cctttcggtt    1200
ctgaaatacc agacgctggc aaaccaaagc ggctacaaag acaaaccgta tgccctgatg    1260
ccgcgccttt ccgccgattg gcgcaaaaac accggcaggg cgcaaatcgg cgtgtccgca    1320
caatttaccc gcttcagcca cgacagccgc caagacggca gccgcctcgt cgtctatccc    1380
gacatcaaat gggatttcag caacagctgg ggttacgtcc gtcccaaact cggactgcac    1440
gccacctatt acagcctcaa ccgcttcggc agccaagaag cccgacgcgt cagccgcact    1500
ctacccatcg tcaacatcga cagcggcatg accttcgaac gcaatacgcg gatgttcggc    1560
ggagaagtcc tgcaaaccct cgagccgcgc ctgttctaca actatattcc tgccaaatcc    1620
caaaacgacc tgcccaattt tgattcgtcg gaaagcagct tcggctacgg gcagcttttt    1680
cgtgaaaacc tctattacgg caacgacagg attaacaccg caaacagcct ttccgccgcc    1740
gtgcaaagcc gtattttgga cggcgcgacg ggggcagagc gtttccgcgc cggcatcggg    1800
cagaaattct acttcaaaaa cgacgcagtc atgcttgacg gcagtgtcgg caaaaaaccg    1860
cgcagccgtt ccgactgggt ggcattcgcc tccagcggca tcggcagccg cttcatcctc    1920
gacagcagca tccactacaa ccaaaacgac aaacgcgccg agaactacgc cgtcggtgca    1980
agctaccgtc ccgcacaggg caaagtgctg aacgcccgct acaaatacgg cgcaacgaa     2040
aaaatctacc tgaagtccga cggttcctat ttttacgaca aactcagcca gctcgacctg    2100
tccgcacaat ggccctgac gcgcaacctg tcggccgtcg tccgttacaa ctacggttttt   2160
gaagccaaaa aaccgataga ggtgctggcg ggtgcggaat acaaaagcag ttgcggctgc    2220
```

-continued

```
tggggcgcgg gcgtgtacgc ccaacgctac gttaccggcg aaaacaccta caaaaacgct    2280 gtcttttct cacttcagtt gaaagacctc agcagtgtcg gcagaaaccc cgcagacagg    2340
atggatgtcg ccgttcccgg ctatatcccc gcccactctc tttccgccgg acgcaacaaa    2400
cggccctga                                                             2409
```

<210> SEQ ID NO 4
<211> LENGTH: 802
<212> TYPE: PRT
<213> ORGANISM: Neisseria meningitidis

<400> SEQUENCE: 4

| Met | Ala | Arg | Leu | Phe | Ser | Leu | Lys | Pro | Leu | Val | Leu | Ala | Leu | Gly | Phe |
| 1 | | | | 5 | | | | | 10 | | | | | 15 | |

| Cys | Phe | Gly | Thr | His | Cys | Ala | Ala | Ala | Asp | Ala | Val | Ala | Ala | Glu | Glu |
| | | | 20 | | | | | 25 | | | | | 30 | | |

| Thr | Asp | Asn | Pro | Thr | Ala | Gly | Gly | Ser | Val | Arg | Ser | Val | Ser | Glu | Pro |
| | | 35 | | | | | 40 | | | | | 45 | | | |

| Met | Gln | Pro | Ala | Gly | Leu | Ser | Leu | Gly | Ser | Thr | Cys | Leu | Phe | Cys | Ser |
| 50 | | | | | 55 | | | | | 60 | | | | | |

| Asn | Glu | Ser | Gly | Lys | Pro | Glu | Lys | Thr | Glu | Ser | Ala | Val | Lys | Gly | Ser |
| 65 | | | | 70 | | | | | 75 | | | | | 80 | |

| Gly | Glu | Gly | Pro | Val | Pro | Glu | Asn | His | Thr | Arg | Ile | Val | Ala | Asp | Lys |
| | | | | 85 | | | | | 90 | | | | | 95 | |

| Val | Glu | Gly | Gln | Ser | Gln | Val | Lys | Val | Arg | Ala | Glu | Gly | Gly | Val | Val |
| | | | 100 | | | | | 105 | | | | | 110 | | |

| Val | Glu | Arg | Asn | Arg | Thr | Thr | Leu | Asn | Ala | Asp | Trp | Ala | Asp | Tyr | Asp |
| | | 115 | | | | | 120 | | | | | 125 | | | |

| Gln | Ser | Gly | Asp | Thr | Val | Thr | Val | Gly | Asp | Arg | Phe | Ala | Leu | Gln | Gln |
| 130 | | | | | 135 | | | | | 140 | | | | | |

| Asp | Gly | Thr | Leu | Ile | Arg | Gly | Glu | Thr | Leu | Thr | Tyr | Asn | Leu | Glu | Gln |
| 145 | | | | 150 | | | | | 155 | | | | | 160 | |

| Gln | Thr | Gly | Glu | Ala | His | Asn | Val | Arg | Met | Glu | Thr | Glu | Gln | Gly | Gly |
| | | | | 165 | | | | | 170 | | | | | 175 | |

| Arg | Arg | Leu | Gln | Ser | Val | Ser | Arg | Thr | Ala | Glu | Met | Leu | Gly | Glu | Gly |
| | | | 180 | | | | | 185 | | | | | 190 | | |

| His | Tyr | Lys | Leu | Thr | Glu | Thr | Gln | Phe | Asn | Thr | Cys | Ser | Ala | Gly | Asp |
| | | 195 | | | | | 200 | | | | | 205 | | | |

| Ala | Gly | Trp | Tyr | Val | Lys | Ala | Ala | Ser | Val | Glu | Ala | Asp | Arg | Glu | Lys |
| 210 | | | | | 215 | | | | | 220 | | | | | |

| Gly | Ile | Gly | Val | Ala | Lys | His | Ala | Ala | Phe | Val | Phe | Gly | Gly | Val | Pro |
| 225 | | | | | 230 | | | | | 235 | | | | | 240 |

| Ile | Phe | Tyr | Thr | Pro | Trp | Ala | Asp | Phe | Pro | Leu | Asp | Gly | Asn | Arg | Lys |
| | | | 245 | | | | | 250 | | | | | 255 | | |

| Ser | Gly | Leu | Leu | Val | Pro | Ser | Leu | Ser | Ala | Gly | Ser | Asp | Gly | Val | Ser |
| | | | 260 | | | | | 265 | | | | | 270 | | |

| Leu | Ser | Val | Pro | Tyr | Tyr | Phe | Asn | Leu | Ala | Pro | Asn | Leu | Asp | Ala | Thr |
| | | 275 | | | | | 280 | | | | | 285 | | | |

| Phe | Ala | Pro | Ser | Val | Ile | Gly | Glu | Arg | Gly | Ala | Val | Phe | Asp | Gly | Gln |
| | 290 | | | | | 295 | | | | | 300 | | | | |

| Val | Arg | Tyr | Leu | Arg | Pro | Asp | Tyr | Ala | Gly | Gln | Ser | Asp | Leu | Thr | Trp |
| 305 | | | | | 310 | | | | | 315 | | | | | 320 |

| Leu | Pro | His | Asp | Lys | Lys | Ser | Gly | Arg | Asn | Asn | Arg | Tyr | Gln | Ala | Lys |
| | | | 325 | | | | | 330 | | | | | 335 | | |

-continued

```
Trp Gln His Arg His Asp Ile Ser Asp Thr Leu Gln Ala Gly Val Asp
            340                 345                 350

Phe Asn Gln Val Ser Asp Ser Gly Tyr Tyr Arg Asp Phe Tyr Gly Asn
            355                 360                 365

Lys Glu Ile Ala Gly Asn Val Asn Leu Asn Arg Arg Val Trp Leu Asp
            370                 375                 380

Tyr Gly Gly Arg Ala Ala Gly Gly Ser Leu Asn Ala Gly Leu Ser Val
385                 390                 395                 400

Leu Lys Tyr Gln Thr Leu Ala Asn Gln Ser Gly Tyr Lys Asp Lys Pro
            405                 410                 415

Tyr Ala Leu Met Pro Arg Leu Ser Ala Asp Trp Arg Lys Asn Thr Gly
            420                 425                 430

Arg Ala Gln Ile Gly Val Ser Ala Gln Phe Thr Arg Phe Ser His Asp
            435                 440                 445

Ser Arg Gln Asp Gly Ser Arg Leu Val Val Tyr Pro Asp Ile Lys Trp
            450                 455                 460

Asp Phe Ser Asn Ser Trp Gly Tyr Val Arg Pro Lys Leu Gly Leu His
465                 470                 475                 480

Ala Thr Tyr Tyr Ser Leu Asn Arg Phe Gly Ser Gln Glu Ala Arg Arg
            485                 490                 495

Val Ser Arg Thr Leu Pro Ile Val Asn Ile Asp Ser Gly Met Thr Phe
            500                 505                 510

Glu Arg Asn Thr Arg Met Phe Gly Gly Glu Val Leu Gln Thr Leu Glu
            515                 520                 525

Pro Arg Leu Phe Tyr Asn Tyr Ile Pro Ala Lys Ser Gln Asn Asp Leu
            530                 535                 540

Pro Asn Phe Asp Ser Ser Glu Ser Ser Phe Gly Tyr Gly Gln Leu Phe
545                 550                 555                 560

Arg Glu Asn Leu Tyr Tyr Gly Asn Asp Arg Ile Asn Thr Ala Asn Ser
            565                 570                 575

Leu Ser Ala Ala Val Gln Ser Arg Ile Leu Asp Gly Ala Thr Gly Ala
            580                 585                 590

Glu Arg Phe Arg Ala Gly Ile Gly Gln Lys Phe Tyr Phe Lys Asn Asp
            595                 600                 605

Ala Val Met Leu Asp Gly Ser Val Gly Lys Lys Pro Arg Ser Arg Ser
            610                 615                 620

Asp Trp Val Ala Phe Ala Ser Ser Gly Ile Gly Ser Arg Phe Ile Leu
625                 630                 635                 640

Asp Ser Ser Ile His Tyr Asn Gln Asn Asp Lys Arg Ala Glu Asn Tyr
            645                 650                 655

Ala Val Gly Ala Ser Tyr Arg Pro Ala Gln Gly Lys Val Leu Asn Ala
            660                 665                 670

Arg Tyr Lys Tyr Gly Arg Asn Glu Lys Ile Tyr Leu Lys Ser Asp Gly
            675                 680                 685

Ser Tyr Phe Tyr Asp Lys Leu Ser Gln Leu Asp Leu Ser Ala Gln Trp
            690                 695                 700

Pro Leu Thr Arg Asn Leu Ser Ala Val Val Arg Tyr Asn Tyr Gly Phe
705                 710                 715                 720

Glu Ala Lys Lys Pro Ile Glu Val Leu Ala Gly Ala Glu Tyr Lys Ser
            725                 730                 735

Ser Cys Gly Cys Trp Gly Ala Gly Val Tyr Ala Gln Arg Tyr Val Thr
            740                 745                 750
```

```
Gly Glu Asn Thr Tyr Lys Asn Ala Val Phe Phe Ser Leu Gln Leu Lys
        755                 760                 765

Asp Leu Ser Ser Val Gly Arg Asn Pro Ala Asp Arg Met Asp Val Ala
        770                 775                 780

Val Pro Gly Tyr Ile Pro Ala His Ser Leu Ser Ala Gly Arg Asn Lys
785                 790                 795                 800

Arg Pro

<210> SEQ ID NO 5
<211> LENGTH: 2016
<212> TYPE: DNA
<213> ORGANISM: Neisseria meningitidis

<400> SEQUENCE: 5
```

| | | | | | |
|---|---|---|---|---|---|
| atgaaactcg | aagcaagcaa | gcaagcaagc | aagcagaagt | ttaaaaaatc | atttattata |   60 |
| agtctatttt | tttctattct | ttatacctct | ccgcttttgg | ctgttgatta | cgtttacgac |  120 |
| aaaaccaagc | tcactgatga | tgaaattacc | cgcttaaaaa | aactccgcga | tagaaatagt |  180 |
| gaatattgga | agaagaaac  | ttatcacata | aaaagtaaca | accgagttta | tccaaacatt |  240 |
| cccgcattat | tccctaaaca | tcctttcgat | ccattcgaaa | acatcaataa | ttcaaaaagg |  300 |
| atttcttttt | atgacaaaga | atacactgaa | gattaccttg | ttggttttgc | tcaaggttta |  360 |
| ggcgttgcaa | aaagaaatgg | ggaaacagaa | aaaccaatac | ggcaatatt  | taaggaatgt |  420 |
| ttaaacactg | ggaaatatag | tgatgatact | tgcaaatctc | aacaatctat | tcctacagta |  480 |
| agaagtgata | ttttcgccct | aaatacgaaa | ataaaaaata | gccatatcaa | cagcgaaatt |  540 |
| ttcgctgtcg | gtaattatac | aaaattgatg | tactcagccc | aacatcattc | tatttggtca |  600 |
| gagcatctct | attccaattc | agaattatct | cttgacgttg | ataactcaca | cgttatcgga |  660 |
| caaacgattg | atttgggagc | attagaatta | acaaattctc | tatgggaacc | ccgttggaac |  720 |
| tctaatattg | attatttaat | aacaaaaaat | gctgaaattc | gttttaacac | taaaagtgaa |  780 |
| agtttactcg | taaaagaaga | ttatgctggc | ggagctcgtt | ttcgttttgc | ttacggtcta |  840 |
| aaagataaag | tccctgaaac | accaattta  | acttttgaaa | aaaatataac | tggcacatca |  900 |
| gatattattt | ttgagggaaa | agcgttggat | aatttaaaac | acctagacgg | gcatcaaatt |  960 |
| atcaaagtaa | atggcacagc | agataaaac  | gcattccgtc | tttctggcaa | acaccaaaag | 1020 |
| ggaatttata | cgctttcttt | acaacaacgc | ccagagggct | tttttaccaa | agtgcaagaa | 1080 |
| cgcgatgata | ttgcgattta | tgcacaacaa | gcccaagccg | ccaatacctt | attcgccttg | 1140 |
| cgtttaaacg | acaaaaacag | cgatattttt | gaccgcactt | taccgcgcaa | aggcttgtgg | 1200 |
| ttacgtgtga | ttgacggaca | ttccagccaa | tgggtacaag | gcaaaacggc | accagtagaa | 1260 |
| ggaaatcgta | aaggcataca | acttggtggc | gatgttttct | cattgcaaaa | tcacaactat | 1320 |
| caactttccg | ttggcttaat | gggcggacaa | gcagaacaac | gcagtacttt | ccgcaaccca | 1380 |
| gatacagaca | atcttacaac | gggaaatgtg | aaaggctttg | gtgcaggcgt | ttacgccact | 1440 |
| tggcatcagc | ttcaggacaa | acagacaggt | gcgtatgcgg | atagctgggt | acaatatcaa | 1500 |
| cgtttccgcc | accgtatcaa | cactgaagat | ggtacagaac | gttttacttc | aaaaggtatt | 1560 |
| actgcctcaa | ttgaagcagg | ttacaacgct | ttattggcgg | aacacgtaac | taaaagggc  | 1620 |
| aacagccttc | gtgtttacct | acaaccacag | gcgcaattga | cttatttggg | ggtaaacgga | 1680 |
| aaattcagcg | atagcgaaaa | tgcccacgtg | aatttacttg | gctctcgcca | attcaaagc  | 1740 |
| cgagtgggcg | ttcaagctaa | agctcaattt | gctttcacta | atggcgtcac | tttccaacca | 1800 |

```
tttgtttccg tcaattcaat ctaccaacaa aaacctttcg gggtagaaat ggacggagaa    1860
cgtcgagtga taaacaacaa aaccgcgatt gaaagccaat taggcgttgc ggtaaaaatt    1920
aaatctcact taactttaca agcaacattc aaccgccaaa caggcaaaca tcatcaagct    1980
aaacaaggcg cattgaattt acagtggacg ttttaa                             2016
```

<210> SEQ ID NO 6
<211> LENGTH: 671
<212> TYPE: PRT
<213> ORGANISM: Neisseria meningitidis

<400> SEQUENCE: 6

```
Met Lys Leu Glu Ala Ser Lys Gln Ala Ser Lys Gln Lys Phe Lys Lys
 1               5                  10                  15

Ser Phe Ile Ile Ser Leu Phe Phe Ser Ile Leu Tyr Thr Ser Pro Leu
                20                  25                  30

Leu Ala Val Asp Tyr Val Tyr Asp Lys Thr Lys Leu Thr Asp Asp Glu
            35                  40                  45

Ile Thr Arg Leu Lys Lys Leu Arg Asp Arg Asn Ser Glu Tyr Trp Lys
        50                  55                  60

Glu Glu Thr Tyr His Ile Lys Ser Asn Asn Arg Val Tyr Pro Asn Ile
 65                  70                  75                  80

Pro Ala Leu Phe Pro Lys His Pro Phe Asp Pro Phe Glu Asn Ile Asn
                 85                  90                  95

Asn Ser Lys Arg Ile Ser Phe Tyr Asp Lys Glu Tyr Thr Glu Asp Tyr
            100                 105                 110

Leu Val Gly Phe Ala Gln Gly Leu Gly Val Ala Lys Arg Asn Gly Glu
        115                 120                 125

Thr Glu Lys Pro Ile Arg Gln Tyr Phe Lys Glu Cys Leu Asn Thr Gly
    130                 135                 140

Lys Tyr Ser Asp Asp Thr Cys Lys Ser Gln Gln Ser Ile Pro Thr Val
145                 150                 155                 160

Arg Ser Asp Ile Phe Ala Leu Asn Thr Lys Ile Lys Asn Ser His Ile
                165                 170                 175

Asn Ser Glu Ile Phe Ala Val Gly Asn Tyr Thr Lys Leu Met Tyr Ser
            180                 185                 190

Ala Gln His His Ser Ile Trp Ser Glu His Leu Tyr Ser Asn Ser Glu
        195                 200                 205

Leu Ser Leu Asp Val Asp Asn Ser His Val Ile Gly Gln Thr Ile Asp
    210                 215                 220

Leu Gly Ala Leu Glu Leu Thr Asn Ser Leu Trp Glu Pro Arg Trp Asn
225                 230                 235                 240

Ser Asn Ile Asp Tyr Leu Ile Thr Lys Asn Ala Glu Ile Arg Phe Asn
                245                 250                 255

Thr Lys Ser Glu Ser Leu Leu Val Lys Glu Asp Tyr Ala Gly Gly Ala
            260                 265                 270

Arg Phe Arg Phe Ala Tyr Gly Leu Lys Asp Lys Val Pro Glu Thr Pro
        275                 280                 285

Ile Leu Thr Phe Glu Lys Asn Ile Thr Gly Thr Ser Asp Ile Ile Phe
    290                 295                 300

Glu Gly Lys Ala Leu Asp Asn Leu Lys His Leu Asp Gly His Gln Ile
305                 310                 315                 320

Ile Lys Val Asn Gly Thr Ala Asp Lys His Ala Phe Arg Leu Ser Gly
                325                 330                 335
```

```
Lys His Gln Lys Gly Ile Tyr Thr Leu Ser Leu Gln Gln Arg Pro Glu
            340                 345                 350
Gly Phe Phe Thr Lys Val Gln Glu Arg Asp Asp Ile Ala Ile Tyr Ala
                355                 360                 365
Gln Gln Ala Gln Ala Ala Asn Thr Leu Phe Ala Leu Arg Leu Asn Asp
            370                 375                 380
Lys Asn Ser Asp Ile Phe Asp Arg Thr Leu Pro Arg Lys Gly Leu Trp
385                 390                 395                 400
Leu Arg Val Ile Asp Gly His Ser Ser Gln Trp Val Gln Gly Lys Thr
                405                 410                 415
Ala Pro Val Glu Gly Asn Arg Lys Gly Ile Gln Leu Gly Gly Asp Val
            420                 425                 430
Phe Ser Leu Gln Asn His Asn Tyr Gln Leu Ser Val Gly Leu Met Gly
            435                 440                 445
Gly Gln Ala Glu Gln Arg Ser Thr Phe Arg Asn Pro Asp Thr Asp Asn
450                 455                 460
Leu Thr Thr Gly Asn Val Lys Gly Phe Gly Ala Gly Val Tyr Ala Thr
465                 470                 475                 480
Trp His Gln Leu Gln Asp Lys Gln Thr Gly Ala Tyr Ala Asp Ser Trp
                485                 490                 495
Val Gln Tyr Gln Arg Phe Arg His Arg Ile Asn Thr Glu Asp Gly Thr
            500                 505                 510
Glu Arg Phe Thr Ser Lys Gly Ile Thr Ala Ser Ile Glu Ala Gly Tyr
            515                 520                 525
Asn Ala Leu Leu Ala Glu His Val Thr Lys Lys Gly Asn Ser Leu Arg
            530                 535                 540
Val Tyr Leu Gln Pro Gln Ala Gln Leu Thr Tyr Leu Gly Val Asn Gly
545                 550                 555                 560
Lys Phe Ser Asp Ser Glu Asn Ala His Val Asn Leu Leu Gly Ser Arg
                565                 570                 575
Gln Leu Gln Ser Arg Val Gly Val Gln Ala Lys Ala Gln Phe Ala Phe
            580                 585                 590
Thr Asn Gly Val Thr Phe Gln Pro Phe Val Ser Val Asn Ser Ile Tyr
            595                 600                 605
Gln Gln Lys Pro Phe Gly Val Glu Met Asp Gly Glu Arg Arg Val Ile
            610                 615                 620
Asn Asn Lys Thr Ala Ile Glu Ser Gln Leu Gly Val Ala Val Lys Ile
625                 630                 635                 640
Lys Ser His Leu Thr Leu Gln Ala Thr Phe Asn Arg Gln Thr Gly Lys
                645                 650                 655
His His Gln Ala Lys Gln Gly Ala Leu Asn Leu Gln Trp Thr Phe
            660                 665                 670

<210> SEQ ID NO 7
<211> LENGTH: 2076
<212> TYPE: DNA
<213> ORGANISM: Neisseria meningitidis

<400> SEQUENCE: 7
atgacactga aagcaagcaa gcaagcaagc ggtcgggtta atctattaac attatctgtt      60
ttatcgctgt tttgcacgcc atatgtttgt ggttcggatg cgtacgatcc cgtcaaagaa     120
gccgagatta aaacaaaatt tattttagaa gcggcggaag acagaaattc ccacgtttgg     180
cgcggcccgt gcagcatatc ttttgattgc ttcggtatgt tcagagctca gcttggttca     240
```

-continued

```
aatactcgtt ctaccaaaat cggcgacgat gccgattttt cattttcaga caagccgaaa    300
cccggcactt cccattattt ttccagcggt aaaaccgatc aaaattcatc cgaatatggg    360
tatgacgaaa tcaatatcca aggtaaaaac tacaatagcg gcatactcgc cgtcgataat    420
atgcccgttg ttaagaaata tattacagat acttacgggg ataatttaaa ggatgcggtt    480
aagaagcaat tacaggattt atacaaaaca gacccgaag cttgggaaga aaataaaaaa    540
cggactgagg aggcgtatat agaacagctt ggaccaaaat ttagtatact caaacagaaa    600
aaccccgatt taattaataa attggtagaa gattccgtac tcactcctca tagtaataca    660
tcacagacta gtctcaacaa catcttcaat aaaaaattac acgtcaaaat cgaaaacaaa    720
tcccacgtcg ccggacaggt gttggaactg accaagatga cgctgaaaga ttccctttgg    780
gaaccgcgcc gccattccga catccatacg ctggaaactt ccgataatgc ccgcatccgc    840
ctgaacacga aagatgaaaa actgaccgtc cataaagcgt atcagggcgg cgcggatttc    900
ctgttcggct acgacgtgcg ggagtcggac gaacccgccc tgacctttga acaaaacgtc    960
agcggaaaat ccggcgtggt tttggaacgc cggccggaaa atctgaaaac gctcgacggg   1020
cgcaaactga ttgcggcgga aaaggcagac cctaattcgt ttgcgtttaa acaaaattac   1080
cggcagggac tgtacgaatt attgctcaag caatgcgaag gcggattttg cttgggtgtg   1140
cagcgtttgg ctatccctga gcggaagcg gttttatatg cccaacaggc ttatgcggca   1200
aatactttgt ttgggctgcg tgccgccgac aggggcgacg acgtgtatgc cgccgatccg   1260
tcccgtcaaa aattgtggct gcgcttcatc ggcggccggt cgcatcaaaa tatacggggc   1320
ggcgcggctg cggacgggcg gcgcaaaggc gtgcaaatcg gcggtgaggt gtttgtacgg   1380
caaaatgaag gcagtcggct ggcaatcggc gtgatgggcg gcagggctgg ccagcacgca   1440
tcagtcaacg gcaaaggcgg tgcggcaggc agttatttgc atggttatgg cggggtgtt   1500 tatgctgcgt ggcatcagtt gcgcgataaa caaacgggtg cgtatttgga cggctggttg   1560
caataccaac gtttcaaaca ccgcatcaat gatgaaaacc gtgcggaacg ctacaaaacc   1620
aaaggttgga cggcttctgt cgaaggcggc tacaacgcgc ttgtggcgga aggcgttgtc   1680
ggaaaaggca ataatgtgcg gttttacctg caaccgcagg cgcagtttac ctacttgggc   1740
gtaaacggcg gctttaccga cagcgagggg acggcggtcg gactgctcgg cagcggtcag   1800
tggcaaagcc gcgccggcat tcgggcaaaa acccgttttg ctttgcgtaa cggtgtcaat   1860
cttcagccct tgccgctttt taatgttttg cacaggtcaa aatctttcgg cgtggaaatg   1920
gacggcgaaa aacagacgct ggcaggcagg acggcgctcg aagggcggtt cggcattgaa   1980
gccggttgga aaggccatat gtccgcacgc atcggatacg gcaaaaggac ggacggcgac   2040
aaagaagccg cattgtcgct caaatggctg ttttga                               2076
```

<210> SEQ ID NO 8
<211> LENGTH: 691
<212> TYPE: PRT
<213> ORGANISM: Neisseria meningitidis

<400> SEQUENCE: 8

```
Met Thr Leu Lys Ala Ser Lys Gln Ala Ser Gly Arg Val Asn Leu Leu
 1               5                  10                  15

Thr Leu Ser Val Leu Ser Leu Phe Cys Thr Pro Tyr Val Cys Gly Ser
            20                  25                  30

Asp Ala Tyr Asp Pro Val Lys Glu Ala Glu Ile Lys Asn Lys Phe Ile
        35                  40                  45
```

```
Leu Glu Ala Ala Glu Asp Arg Asn Ser His Val Trp Arg Gly Pro Cys
 50                  55                  60

Ser Ile Ser Phe Asp Cys Phe Gly Met Phe Arg Ala Gln Leu Gly Ser
 65                  70                  75                  80

Asn Thr Arg Ser Thr Lys Ile Gly Asp Asp Ala Asp Phe Ser Phe Ser
                 85                  90                  95

Asp Lys Pro Lys Pro Gly Thr Ser His Tyr Phe Ser Ser Gly Lys Thr
                100                 105                 110

Asp Gln Asn Ser Ser Glu Tyr Gly Tyr Asp Glu Ile Asn Ile Gln Gly
                115                 120                 125

Lys Asn Tyr Asn Ser Gly Ile Leu Ala Val Asp Asn Met Pro Val Val
    130                 135                 140

Lys Lys Tyr Ile Thr Asp Thr Tyr Gly Asp Asn Leu Lys Asp Ala Val
145                 150                 155                 160

Lys Lys Gln Leu Gln Asp Leu Tyr Lys Thr Arg Pro Glu Ala Trp Glu
                165                 170                 175

Glu Asn Lys Lys Arg Thr Glu Glu Ala Tyr Ile Glu Gln Leu Gly Pro
                180                 185                 190

Lys Phe Ser Ile Leu Lys Gln Lys Asn Pro Asp Leu Ile Asn Lys Leu
    195                 200                 205

Val Glu Asp Ser Val Leu Thr Pro His Ser Asn Thr Ser Gln Thr Ser
210                 215                 220

Leu Asn Ile Phe Asn Lys Lys Leu His Val Lys Ile Glu Asn Lys
225                 230                 235                 240

Ser His Val Ala Gly Gln Val Leu Glu Leu Thr Lys Met Thr Leu Lys
                245                 250                 255

Asp Ser Leu Trp Glu Pro Arg Arg His Ser Asp Ile His Thr Leu Glu
                260                 265                 270

Thr Ser Asp Asn Ala Arg Ile Arg Leu Asn Thr Lys Asp Glu Lys Leu
    275                 280                 285

Thr Val His Lys Ala Tyr Gln Gly Gly Ala Asp Phe Leu Phe Gly Tyr
290                 295                 300

Asp Val Arg Glu Ser Asp Glu Pro Ala Leu Thr Phe Glu Gln Asn Val
305                 310                 315                 320

Ser Gly Lys Ser Gly Val Val Leu Glu Arg Arg Pro Glu Asn Leu Lys
                325                 330                 335

Thr Leu Asp Gly Arg Lys Leu Ile Ala Ala Glu Lys Ala Asp Pro Asn
                340                 345                 350

Ser Phe Ala Phe Lys Gln Asn Tyr Arg Gln Gly Leu Tyr Glu Leu Leu
    355                 360                 365

Leu Lys Gln Cys Glu Gly Gly Phe Cys Leu Gly Val Gln Arg Leu Ala
    370                 375                 380

Ile Pro Glu Ala Glu Ala Val Leu Tyr Ala Gln Gln Ala Tyr Ala Ala
385                 390                 395                 400

Asn Thr Leu Phe Gly Leu Arg Ala Ala Asp Arg Gly Asp Asp Val Tyr
                405                 410                 415

Ala Ala Asp Pro Ser Arg Gln Lys Leu Trp Leu Arg Phe Ile Gly Gly
                420                 425                 430

Arg Ser His Gln Asn Ile Arg Gly Ala Ala Asp Gly Arg Arg
    435                 440                 445

Lys Gly Val Gln Ile Gly Gly Glu Val Phe Val Arg Gln Asn Glu Gly
    450                 455                 460

Ser Arg Leu Ala Ile Gly Val Met Gly Gly Arg Ala Gly Gln His Ala
```

-continued

```
            465                 470                 475                 480
Ser Val Asn Gly Lys Gly Gly Ala Ala Gly Ser Tyr Leu His Gly Tyr
                    485                 490                 495

Gly Gly Gly Val Tyr Ala Ala Trp His Gln Leu Arg Asp Lys Gln Thr
                500                 505                 510

Gly Ala Tyr Leu Asp Gly Trp Leu Gln Tyr Gln Arg Phe Lys His Arg
            515                 520                 525

Ile Asn Asp Glu Asn Arg Ala Glu Arg Tyr Lys Thr Lys Gly Trp Thr
        530                 535                 540

Ala Ser Val Glu Gly Gly Tyr Asn Ala Leu Val Ala Glu Gly Val Val
545                 550                 555                 560

Gly Lys Gly Asn Asn Val Arg Phe Tyr Leu Gln Pro Gln Ala Gln Phe
                565                 570                 575

Thr Tyr Leu Gly Val Asn Gly Gly Phe Thr Asp Ser Glu Gly Thr Ala
                580                 585                 590

Val Gly Leu Leu Gly Ser Gly Gln Trp Gln Ser Arg Ala Gly Ile Arg
            595                 600                 605

Ala Lys Thr Arg Phe Ala Leu Arg Asn Gly Val Asn Leu Gln Pro Phe
        610                 615                 620

Ala Ala Phe Asn Val Leu His Arg Ser Lys Ser Phe Gly Val Glu Met
625                 630                 635                 640

Asp Gly Glu Lys Gln Thr Leu Ala Gly Arg Thr Ala Leu Glu Gly Arg
                645                 650                 655

Phe Gly Ile Glu Ala Gly Trp Lys Gly His Met Ser Ala Arg Ile Gly
                660                 665                 670

Tyr Gly Lys Arg Thr Asp Gly Asp Lys Glu Ala Ala Leu Ser Leu Lys
            675                 680                 685

Trp Leu Phe
    690
```

COMPOUNDS

FIELD OF THE INVENTION

This invention relates to polynucleotides, (herein referred to as "BASB047 polynucleotide(s)", "BASB054 polynucleotide(s)", "BASB068 polynucleotide(s)" and "BASB069 polynucleotide(s)"), polypeptides encoded by them (referred to herein as "BASB047", "BASB054", "BASB068" and "BASB069" respectively or "BASB047 polypeptide(s)", "BASB054 polypeptide(s)", "BASB068 polypeptide(s)" and "BASB069 polypeptide(s)" respectively), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens.

BACKGROUND OF THE INVENTION

*Neisseria meningitidis* (meningococcus) is a Gram-negative bacterium frequently isolated from the human upper respiratory tract. It occasionally causes invasive bacterial diseases such as bacteremia and meningitis. The incidence of meningococcal disease shows geographical seasonal and annual differences (Schwartz, B., Moore, P. S., Broome, C. V.; Clin. Microbiol. Rev. 2 (Supplement), S18–S24, 1989). Most disease in temperate countries is due to strains of serogroup B and varies in incidence from 1–10/100,0001/year total population sometimes reaching higher values (Kaczmarski, E. B. (1997), Commun. Dis. Rep. Rev. 7: R55–9, 1995; Scholten, R. J. P. M., Bijlmer, H. A., Poolman, J. T. et al. Clin. Infect. Dis. 16: 237–246, 1993; Cruz, C., Pavez, G., Aguilar, E., et al. Epidemiol. Infect. 105: 119–126, 1990).

Epidemics dominated by serogroup A meningococci, mostly in central Africa, are encountered, sometimes reaching levels up to 1000/100,000/year (Schwartz, B., Moore, P. S., Broome, C. V. Clin. Microbiol. Rev. 2 (Supplement), S18–S24, 1989). Nearly all cases as a whole of meningococcal disease are caused by serogroup A, B, C, W-135 and Y meningococci and a tetravalent A, C, W-135, Y polysaccharide vaccine is available (Armand, J., Arminjon, F., Mynard, M. C., Lafaix, C., J. Biol. Stand. 10: 335–339, 1982).

The polysaccharide vaccines are currently being improved by way of chemical conjugating them to carrier proteins (Lieberman, J. M., Chiu, S. S., Wong, V. K., et al. JAMA 275: 1499–1503, 1996).

A serogroup B vaccine is not available, since the B capsular polysaccharide was found to be nonimmunogenic, most likely because it shares structural similarity to host components (Wyle, F. A., Artenstein, M. S., Brandt, M. L. et al. J. Infect. Dis. 126: 514–522, 1972; Finne, J. M., Leinonen, M., Mäkelä, P. M. Lancet ii.: 355–357, 1983).

For many years efforts have been initiated and carried out to develop meningococcal outer membrane based vaccines (de Moraes, J. C., Perkins, B., Carnargo, M. C. et al. Lancet 340: 1074–1078, 1992; Bjune, G., Hoiby, E. A. Gronnesby, J. K. et al. 338: 1093–1096, 1991). Such vaccines have demonstrated efficacies from 57%–85% in older children (>4 years) and adolescents.

Many bacterial outer membrane components are present in these vaccines, such as PorA, PorB, Rmp, Opc, Opa, FrpB and the contribution of these components to the observed protection still needs father definition. Other bacterial outer membrane components have been defined by using animal or human antibodies to be potentially relevant to the induction of protective immunity, such as TbpB and NspA (Martin, D., Cadieux, N., Hamel, J., Brodeux, B. R., J. Exp. Med. 185: 1173–1183, 1997; Lissolo, L., Maitre-Wilmotte, C., Dumas, p. et al., Inf. Immun. 63: 884–890, 1995). The mechanisms of protective immunity will involve antibody mediated bactericidal activity and opsonophagocytosis.

A bacteremia animal model has been used to combine all antibody mediated mechanisms (Saukkonen. K., Leinonen. M., Abdillahi. H. Poolman. J. T. Vaccine 7: 325–328. 1989). It is generally accepted that the late complement component mediated bactericidal mechanism is crucial for immunity against meningococcal disease (Ross, S. C., Rosenthal P. J., Berberic, H. M., Densen, P. J. Infect. Dis. 155: 1266–1275, 1987).

The frequency of *Neisseria meningitidis* infections has risen dramatically in the past few decades. This has been attributed to the emergence of multiply antibiotic resistant strains and an increasing population of people with weakened immune systems. It is no longer uncommon to isolate *Neisseria meningitidis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB047, BASB054, BASB068 and BASB069, in particular BASB047, BASB054, BASB068 and BASB069 polypeptides and BASB047, BASB054, BASB068 and BASB069 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB047, BASB054, BASB068 and BASB069 polynucleotides or polypeptides.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to BASB047, BASB054, BASB068 and BASB069 polypeptides and polynucleotides as described in greater detail below. The invention relates especially to BASB047, BASB054, BASB068 and BASB069 having the nucleotide and amino acid sequences set out in SEQ ID NO:1,3,5,7 and SEQ ID NO:2,4,6,8 respectively. It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Polypeptides

In one aspect of the invention there are provided polypeptides of *Neisseria meningitidis* referred to herein as "BASB047", "BASB054", "BASB068" and "BASB069", and "BASB047 polypeptides", "BASB054 polypeptides", "BASB068 polypeptides" and "BASB069 polypeptides" as well as biologically, diagnostically, prophylactically, clinically or therapeutically useful variants thereof, and compositions comprising the same.

The present invention further provides for:

(a) an isolated polypeptide which comprises an amino acid sequence which has at least 85% identity, more preferably at least 90% identity, yet more preferably at least 95% identity, most preferably at least 97–99% or exact identity, to that of SEQ ID NO:2.

(b) a polypeptide encoded by an isolated polynucleotide comprising a polynucleotide sequence which has at least 85% identity, more preferably at least 90% identity, yet more preferably at least 95% identity, even more preferably at least 97–99% or exact identity to SEQ ID NO:1 over the entire length of SEQ ID NO:1.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97–99% or exact identity, to the amino acid sequence of SEQ ID NO:2.

The BASB043 polypeptide provided in SEQ ID NO:2 is the BASB047 polypeptide from *Neisseria meningitidis* strain ATCC13090.

The invention also provides an immunogenic fragment of a BASB047 polypeptide, that is, a contiguous portion of the BASB047 polypeptide which has the same or substantially the same immunogenic activity as the polypeptide comprising the amino acid sequence of SEQ ID NO:2. That is to say, the fragment (if necessary when coupled to a carrier) is capable of raising an immune response which recognises the BASB047 polypeptide. Such an immunogenic fragment may include, for example, the BASB047 polypeptide lacking an N-terminal leader sequence, and/or a transmembrane domain and/or a C-terminal anchor domain. In a preferred aspect the immunogenic fragment of BASB047 according to the invention comprises substantially all of the extracellular domain of a polypeptide which has at least 85% identity, more preferably at least 90% identity, yet more preferably at least 95% identity, most preferably at least 97–99% identity, to that of SEQ ID NO:2 over the entire length of SEQ ID NO:2.

The present invention further provides for:

(a) an isolated polypeptide which comprises an amino acid sequence which has at least 85% identity, more preferably at least 90% identity, yet more preferably at least 95% identity, most preferably at least 97–99% or exact identity, to that of SEQ ID NO:4.

(b) a polypeptide encoded by an isolated polynucleotide comprising a polynucleotide sequence which has at least 85% identity, more preferably at least 90% identity, yet more preferably at least 95% identity, even more preferably at least 97–99% or exact identity to SEQ ID NO:3 over the entire length of SEQ ID NO:3.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97–99% or exact identity, to the amino acid sequence of SEQ ID NO:4

The BASB054 polypeptide provided in SEQ ID NO:4 is the BASB054 polypeptide from *Neisseria meningitidis* strain ATCC13090.

The invention also provides an immunogenic fragment of a BASB054 polypeptide, that is, a contiguous portion of the BASB054 polypeptide which has the same or substantially the same immunogenic activity as the polypeptide comprising the amino acid sequence of SEQ ID NO:4. That is to say, the fragment (if necessary when coupled to a carrier) is capable of raising an immune response which recognises the BASB054 polypeptide. Such an immunogenic fragment may include, for example, the BASB054 polypeptide lacking an N-terminal leader sequence, and/or a transmembrane domain and/or a C-terminal anchor domain. In a preferred aspect the immunogenic fragment of BASB054 according to the invention comprises substantially all of the extracellular domain of a polypeptide which has at least 85% identity, more preferably at least 90% identity, yet more preferably at least 95% identity, most preferably at least 97–99% identity, to that of SEQ ID NO:4 over the entire length of SEQ ID NO:4.

The present invention further provides for:

(a) an isolated polypeptide which comprises an amino acid sequence which has at least 85% identity, more preferably at least 90% identity, yet more preferably at least 95% identity, most preferably at least 97–99% or exact identity, to that of SEQ ID NO:6.

(b) a polypeptide encoded by an isolated polynucleotide comprising a polynucleotide sequence which has at least 85% identity, more preferably at least 90% identity, yet more preferably at least 95% identity, even more preferably at least 97–99% or exact identity to SEQ ID NO:5 over the entire length of SEQ ID NO:5.

c) a polypeptide encoded by an isolated polynucleotide comprising a polynucleotide sequence encoding a polypeptide which has at least 85% identity, more preferably at least 90% identity, yet more preferably at least 95% identity, even more preferably at least 97–99% or exact identity, to the amino acid sequence of SEQ ID NO:6

The BASB068 polypeptide provided in SEQ ID NO:6 is the BASB068 polypeptide from *Neisseria meningitidis* strain ATCC13090.

The invention also provides an immunogenic fragment of a BASB068 polypeptide, that is, a contiguous portion of the BASB068 polypeptide which has the same or substantially the same immunogenic activity as the polypeptide comprising the amino acid sequence of SEQ ID NO:6. That is to say, the fragment (if necessary when coupled to a carrier) is capable of raising an immune response which recognises the BASB068 polypeptide. Such an immunogenic fragment may include, for example, the BASB068 polypeptide lacking an N-terminal leader sequence, and/or a transmembrane domain and/or a C-terminal anchor domain. In a preferred aspect the immunogenic fragment of BASB068 according to the invention comprises substantially all of the extracellular domain of a polypeptide which has at least 85% identity, more preferably at least 90% identity, yet more preferably at least 95% identity, most preferably at least 97–99% identity, to that of SEQ ID NO:6 over the entire length of SEQ ID NO:6.

The present invention further provides for:

(a) an isolated polypeptide which comprises an amino acid sequence which has at least 85% identity, more preferably at least 90% identity, yet more preferably at least 95% identity, most preferably at least 97–99% or exact identity, to that of SEQ ID NO:8.

(b) a polypeptide encoded by an isolated polynucleotide comprising a polynucleotide sequence which has at least 85% identity, more preferably at least 90% identity, yet more preferably at least 95% identity, even more preferably at least 97–99% or exact identity to SEQ ID NO:7 over the entire length of SEQ ID NO:7.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97–99% or exact identity, to the amino acid sequence of SEQ ID NO:8.

The BASB069 polypeptide provided in SEQ ID NO:8 is the BASB069 polypeptide from *Neisseria meningitidis* strain ATCC13090.

The invention also provides an immunogenic fragment of a BASB069 polypeptide, that is, a contiguous portion of the BASB069 polypeptide which has the same or substantially the same immunogenic activity as the polypeptide comprising the amino acid sequence of SEQ ID NO:8. That is to say, the fragment (if necessary when coupled to a carrier) is capable of raising an immune response which recognises the BASB069 polypeptide. Such an immunogenic fragment may include, for example, the BASB069 polypeptide lacking an N-terminal leader sequence, and/or a transmembrane domain and/or a C-terminal anchor domain. In a preferred aspect the immunogenic fragment of BASB069 according to the invention comprises substantially all of the extracellular domain of a polypeptide which has at least 85% identity, more preferably at least 90% identity, yet more preferably at least 95% identity, most preferably at least 97–99% identity, to that of SEQ ID NO:8 over the entire length of SEQ ID NO:8.

A fragment is a polypeptide having an amino acid sequence that is entirely the same as part but not all of any amino acid sequence of any polypeptide of the invention. As with BASB047, BASB054, BASB068 and BASB069 polypeptides, fragments may be "free-standing", or comprised within a larger polypeptide of which they form a part or region, most preferably as a single continuous region in a single larger polypeptide.

Preferred fragments include, for example, truncation polypeptides having a portion of an amino acid sequence of SEQ ID NO:2,4,6,8 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2,4,6,8 or an isolated polypeptide comprising an amino acid sequence having at least 15, 20, 30, 40, 50 or 100 contiguous amino acids truncated or deleted from the amino acid sequence of SEQ ID NO:2,4, 6,8.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5–10, 1–5, 1–3, 1–2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor $X_a$.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. If the fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LytA. Preferably the C terminal portion of the molecule is used. LytA is derived from *Streptococcus pneumoniae* which synthesize an N-acetyl-L-alanine amidase, amidase LytA, (coded by the lytA gene {Gene, 43 (1986) page 265–272}) an autolysin that specifically degrades certain bonds in the peptidoglycan backbone. The C-terminal domain of the LvtA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795–798}. It is possible to use the repeat portion of the LytA molecule found in the C terminal end starting at residue 178, for example residues 188–305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gin; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Neisseria meningitidis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB047 polypeptides, particularly polynucleotides that encode the polypeptide herein designated BASB047.

In a particularly preferred embodiment of the invention the polynucleotide comprises a region encoding BASB047 polypeptides comprising a sequence set out in SEQ ID NO:1 which includes a full length gene, or a variant thereof.

The BASB047 polynucleotide provided in SEQ ID NO:1 is the BASB047 polynucleotide from *Neisseria meningitidis* strains ATCC13090.

As a further aspect of the invention there are provided isolated nucleic acid molecules encoding and/or expressing BASB047 polypeptides and polynucleotides, particularly *Neisseria meningitidis* BASB047 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB047 polypeptide having a deduced amino acid sequence of SEQ ID NO:2 and polynucleotides closely related thereto and variants thereof.

In another particularly preferred embodiment of the invention there is a BASB047 polypeptide from *Neisseria meningitidis* comprising or consisting of an amino acid sequence of SEQ ID NO:2 or a variant thereof.

Using the information provided herein, such as a polynucleotide sequence set out in SEQ ID NO:1 a polynucleotide of the invention encoding BASB047 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:1 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULER CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1 was discovered in a DNA library derived from *Neisseria meningitidis*.

Moreover, the DNA sequence set out in SEQ ID NO:1 contains an open reading frame encoding a protein having about the number of amino acid residues set forth in SEQ ID NO:2 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 1201 of SEQ ID NO:1, encodes the polypeptide of SEQ ID NO:2.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97–99% or exact identity to SEQ ID NO:1 over the entire length of SEQ ID NO:1; or (b) a polynucleotide sequence encoding a polypeptide which has at least 85% identity, more preferably at least 90% identity, yet more preferably at least 95% identity, even more preferably at least 97–99% or 100% exact, to the amino acid sequence of SEQ ID NO:2 over the entire length of SEQ ID NO:2.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45–65° C. and an SDS A concentration from 0.1–1%) with a labeled or detectable probe consisting of or comprising the sequence of SEQ ID NO:1 or a fragment thereof; and isolating a full-length gene and/or genomic clones containing said polynucleotide sequence.

The invention provides a polynucleotide sequence identical over its entire length to a coding sequence (open reading frame) in SEQ ID NO:1. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB047 polypeptide of SEQ ID NO:2 may be identical to the polypeptide encoding sequence contained in nucleotides 1 to 1200 of SEQ ID NO:1. Alternatively it may be a sequence, which as a result of the redundancy (degeneracy) of the genetic code, also encodes the polypeptide of SEQ ID NO:2. The term "polynucleotide encoding a polypeptide" as used herein encompasses polynucleotides that include a sequence encoding a polypeptide of the invention, particularly a bacterial polypeptide and more particularly a polypeptide of the Neisseria meningitidis BASB047 having an amino acid sequence set out in SEQ ID NO:2. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2. Fragments of polynucleotides of the invention may be used, for example, to synthesize full-length polynucleotides of the invention.

Further particularly preferred embodiments are polynucleotides encoding BASB047 variants, that have the amino acid sequence of BASB047 polypeptide of SEQ ID NO:2 in which several, a few, 5 to 10, 1 to 5, 1 to 3, 2, 1 or no amino acid residues are substituted. modified, deleted and/or added, in any combination. Especially preferred among these are silent substitutions, additions and deletions, that do not alter the properties and activities of BASB047 polypeptide.

Further preferred embodiments of the invention are polynucleotides that are at least 85% identical over their entire length to a polynucleotide encoding BASB047 polypeptide having an amino acid sequence set out in SEQ ID NO:2 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1.

In accordance with certain preferred embodiments of this invention there are provided polynucleotides that hybridize, particularly under stringent conditions, to BASB047 polynucleotide sequences, such as those polynucleotides in SEQ ID NO:1.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB047 and to isolate cDNA and genomic clones of other genes that have a high identity, particularly high sequence identity, to the BASB047 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB047 gene may be isolated by screening using a DNA sequence provided in SEQ ID NO:1 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB054 polypeptides, particularly polynucleotides that encode the polypeptide herein designated BASB054.

In a particularly preferred embodiment of the invention the polynucleotide comprises a region encoding BASB054 polypeptides comprising a sequence set out in SEQ ID NO:3 which includes a full length gene, or a variant thereof.

The BASB054 polynucleotide provided in SEQ ID NO:3 is the BASB054 polynucleotide from Neisseria meningitidis strains ATCC13090.

As a further aspect of the invention there are provided isolated nucleic acid molecules encoding and/or expressing BASB054 polypeptides and polynucleotides, particularly Neisseria meningitidis BASB054 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB054 polypeptide having a deduced amino acid sequence of SEQ ID NO:4 and polynucleotides closely related thereto and variants thereof.

In another particularly preferred embodiment of the invention there is a BASB054 polypeptide from *Neisseria meningitidis* comprising or consisting of an amino acid sequence of SEQ ID NO:4 or a variant thereof.

Using the information provided herein, such as a polynucleotide sequence set out in SEQ ID NO:3 a polynucleotide of the invention encoding BASB054 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:3 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:3 was discovered in a DNA library derived from *Neisseria meningitidis.*

Moreover, the DNA sequence set out in SEQ ID NO:3 contains an open reading frame encoding a protein having about the number of amino acid residues set forth in SEQ ID NO:4 with a deduced molecular weight that can be calculated using amino acid residue molecular weight values well known to those skilled in the art.

The polynucleotide of SEQ ID NO:3, between the start codon at nucleotide number 1 and the stop codon which begins at nucleotide number 2407 of SEQ ID NO:3, encodes the polypeptide of SEQ ID NO:4.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97–99% or exact identity to SEQ ID NO:3 over the entire length of SEQ ID NO:3; or (b) a polynucleotide sequence encoding a polypeptide which has at least 85% identity, more preferably at least 90% identity, yet more preferably at least 95% identity, even more preferably at least 97–99% or 100% exact, to the amino acid sequence of SEQ ID NO:4 over the entire length of SEQ ID NO:4.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:3 or a fragment thereof; and isolating a full-length gene and/or genomic clones containing said polynucleotide sequence.

The invention provides a polynucleotide sequence identical over its entire length to a coding sequence (open reading frame) in SEQ ID NO:3. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals.

The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB054 polypeptide of SEQ ID NO:4 may be identical to the polypeptide encoding sequence contained in nucleotides 1 to 2406 of SEQ ID NO:3. Alternatively it may be a sequence, which as a result of the redundancy (degeneracy) of the genetic code, also encodes the polypeptide of SEQ ID NO:4. The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB054 having an amino acid sequence set out in SEQ ID NO:4. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:4. Fragments of polynucleotides of the invention may be used, for example, to synthesize full-length polynucleotides of the invention.

Further particularly preferred embodiments are polynucleotides encoding BASB054 variants, that have the amino acid sequence of BASB054 polypeptide of SEQ ID NO:4 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB054 polypeptide.

Further preferred embodiments of the invention are polynucleotides that are at least 85% identical over their entire length to a polynucleotide encoding BASB054 polypeptide having an amino acid sequence set out in SEQ ID NO:4 and a polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:3.

In accordance with certain preferred embodiments of this invention there are provided polynucleotides that hybridize, particularly under stringent conditions, to BASB054 polynucleotide sequences, such as those polynucleotides in SEQ ID NO:3.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:3 under stringent hybridization conditions with a probe having the sequence of said polynucleotide sequence set forth in SEQ ID NO:3 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB054 and to isolate cDNA and genomic clones of other genes that have a high identity, particularly high sequence identity, to the BASB054 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB054 gene may be isolated by screening using a DNA sequence provided in SEQ ID NO:3 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB068 polypeptides, particularly polynucleotides that encode the polypeptide herein designated BASB068.

In a particularly preferred embodiment of the invention the polynucleotide comprises a region encoding BASB068 polypeptides comprising a sequence set out in SEQ ID NO:5 which includes a full length gene, or a variant thereof.

The BASB068 polynucleotide provided in SEQ ID NO:5 is the BASB068 polynucleotide from *Neisseria meningitidis* strains ATCC13090.

As a further aspect of the invention there are provided isolated nucleic acid molecules encoding and/or expressing BASB068 polypeptides and polynucleotides, particularly *Neisseria meningitidis* BASB068 polypeptides and polynucleotides, including, for example, unprocessed RNAS, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB068 polypeptide having a deduced amino acid sequence of SEQ ID NO:6 and polynucleotides closely related thereto and variants thereof.

In another particularly preferred embodiment of the invention there is a BASB068 polypeptide from *Neisseria meningitidis* comprising or consisting of an amino acid sequence of SEQ ID NO:6 or a variant thereof.

Using the information provided herein, such as a polynucleotide sequence set out in SEQ ID NO:5 a polynucleotide of the invention encoding BASB068 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:5 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:5 was discovered in a DNA library derived from *Neisseria meningitidis.*

Moreover, the DNA sequence set out in SEQ ID NO:5 contains an open reading frame encoding a protein having about the number of amino acid residues set forth in SEQ ID NO:6 with a deduced molecular weight that can be calculated using amino acid residue molecular weight values well known to those skilled in the art.

The polynucleotide of SEQ ID NO:5, between the start codon at nucleotide number 1 and the stop codon which begins at nucleotide number 2014 of SEQ ID NO:5, encodes the polypeptide of SEQ ID NO:6.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97–99% or exact identity to SEQ ID NO:5 over the entire length of SEQ ID NO:5; or (b) a polynucleotide sequence encoding a polypeptide which has at least 85% identity, more preferably at least 90% identity, yet more preferably at least 95% identity, even more preferably at least 97–99% or 100% exact, to the amino acid sequence of SEQ ID NO:6 over the entire length of SEQ ID NO:6.

A polynucleotide encoding a polypeptide of the present invention, including homologs and orthologs from species other than *Neisseria meningitidis,* may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:5 or a fragment thereof; and isolating a full-length gene and/or genomic clones containing said polynucleotide sequence.

The invention provides a polynucleotide sequence identical over its entire length to a coding sequence (open reading frame) in SEQ ID NO:5. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences sequences that stabilize mRNA, introns, and polyadenylation signals.

The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB068 polypeptide of SEQ ID NO:6 may be identical to the polypeptide encoding sequence contained in nucleotides 1 to 2013 of SEQ ID NO:5. Alternatively it may be a sequence, which as a result of the redundancy (degeneracy) of the genetic code, also encodes the polypeptide of SEQ ID NO:6. The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB068 having an amino acid sequence set out in SEQ ID NO:6. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:6. Fragments of polynucleotides of the invention may be used, for example, to synthesize full-length polynucleotides of the invention.

Further particularly preferred embodiments are polynucleotides encoding BASB068 variants, that have the amino acid sequence of BASB068 polypeptide of SEQ ID NO:6 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB068 polypeptide.

Further preferred embodiments of the invention are polynucleotides that are at least 85% identical over their entire length to a polynucleotide encoding BASB068 polypeptide having an amino acid sequence set out in SEQ ID NO:6 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:5.

In accordance with certain preferred embodiments of this invention there are provided polynucleotides that hybridize, particularly under stringent conditions, to BASB068 polynucleotide sequences, such as those polynucleotides in SEQ ID NO:5.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:5 under stringent hybridization conditions with a probe having the sequence of said polynucleotide sequence set forth in SEQ ID NO:5 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB068 and to isolate cDNA and genomic clones of other genes that have a high identity, particularly high sequence identity, to the BASB068 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB068 gene may be isolated by screening using a DNA sequence provided in SEQ ID NO:5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB069 polypeptides, particularly polynucleotides that encode the polypeptide herein designated BASB069.

In a particularly preferred embodiment of the invention the polynucleotide comprises a region encoding BASB069 polypeptides comprising a sequence set out in SEQ ID NO:7 which includes a full length gene, or a variant thereof.

The BASB069 polynucleotide provided in SEQ ID NO:7 is the BASB069 polynucleotide from *Neisseria meningitidis* strains ATCC13090.

As a further aspect of the invention there are provided isolated nucleic acid molecules encoding and/or expressing BASB069 polypeptides and polynucleotides, particularly *Neisseria meningitidis* BASB069 polypeptides and polynucleotides, including, for example, unprocessed RNAs, ribozyme RNAs, mRNAs, cDNAs, genomic DNAs, B- and Z-DNAS. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB069 polypeptide having a deduced amino acid sequence of SEQ ID NO:8 and polynucleotides closely related thereto and variants thereof.

In another particularly preferred embodiment of the invention there is a BASB069 polypeptide from *Neisseria meningitidis* comprising or consisting of an amino acid sequence of SEQ ID NO:8 or a variant thereof.

Using the information provided herein, such as a polynucleotide sequence set out in SEQ ID NO:7 a polynucleotide of the invention encoding BASB069 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:7 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:7 was discovered in a DNA library derived from *Neisseria meningitidis.*

Moreover, the DNA sequence set out in SEQ ID NO:7 contains an open reading frame encoding a protein having about the number of amino acid residues set forth in SEQ ID NO:8 with a deduced molecular weight that can be calculated using amino acid residue molecular weight values well known to those skilled in the art.

The polynucleotide of SEQ ID NO:7, between the start codon at nucleotide number 1 and the stop codon which begins at nucleotide number 2074 of SEQ ID NO:7, encodes the polypeptide of SEQ ID NO:8.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97–99% or exact identity to SEQ ID NO:7 over the entire length of SEQ ID NO:7; or (b) a polynucleotide sequence encoding a polypeptide which has at least 85% identity, more preferably at least 90% identity, yet more preferably at least 95% identity, even more preferably at least 97–99% or 100% exact, to the amino acid sequence of SEQ ID NO:8 over the entire length of SEQ ID NO:8.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:7 or a fragment thereof; and isolating a full-length gene and/or genomic clones containing said polynucleotide sequence.

The invention provides a polynucleotide sequence identical over its entire length to a coding sequence (open reading frame) in SEQ ID NO:7. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences. sequences that stabilize mRNA, introns, and polyadenylation signals.

The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB069 polypeptide of SEQ ID NO:8 may be identical to the polypeptide encoding sequence contained in nucleotides 1 to 2073 of SEQ ID NO:7. Alternatively it may be a sequence, which as a result of the redundancy (degeneracy) of the genetic code, also encodes the polypeptide of SEQ ID NO:8. The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB069 having an amino acid sequence set out in SEQ ID NO:8. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:8. Fragments of polynucleotides of the invention may be used, for example, to synthesize full-length polynucleotides of the invention.

Further particularly preferred embodiments are polynucleotides encoding BASB069 variants, that have the amino acid sequence of BASB069 polypeptide of SEQ ID NO:8 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB069 polypeptide.

Further preferred embodiments of the invention are polynucleotides that are at least 85% identical over their entire length to a polynucleotide encoding BASB069 polypeptide having an amino acid sequence set out in SEQ ID NO:8 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:7.

In accordance with certain preferred embodiments of this invention there are provided polynucleotides that hybridize, particularly under stringent conditions, to BASB069 polynucleotide sequences, such as those polynucleotides in SEQ ID NO:7.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:7 under stringent hybridization conditions with a probe having the sequence of said polynucleotide sequence set forth in SEQ ID NO:7 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB069 and to isolate cDNA and genomic clones of other genes that have a high identity, particularly high sequence identity, to the BASB069 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB069 gene may be isolated by screening using a DNA sequence provided in SEQ ID NO:7 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NOS:1–8 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther.* (1983) 4: 419), delivery of DNA complexed with specific protein carriers (Wu et al., *J. Biol Chem.* (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, E. coli, streptomyces, cyanobacteria, Bacillus subtilis, Moraxella cotarrhalis, Haemophilus influenzae and Neisseria meningitidis; fungal cells, such as cells of a yeast, Kluveromyces, Saccharomyces, a basidiomycete, Candida albicans and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g.; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), Listeria, Salmonella, Shigella, Neisseria, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of BASB047, BASB054, BASB068 or BASB069 polynucleotides and polypeptides of the invention for use as diagnostic reagents. Detection of BASB047, BASB054, BASB068 or BASB069 polynucleotides and/or polypeptides in a eukaryote, particularly a mammals, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB047, BASB054, BASB068 or BASB069 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB047, BASB054, BASB068 or BASB069 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., Science, 230: 1242 (1985). Sequence changes at specific locations also may be revealed by nuclease protection assays, such as RNase, V1 and S1 protection assay or a chemical cleavage method. See, for example, Cotton et al., Proc. Natl. Acad Sci, USA, 85: 4397–4401 (1985).

In another embodiment, an array of oligonucleotides probes comprising a BASB047, BASB054, BASB068 or BASB069 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., Science, 274: 610 (1996)).

Thus in another aspect, the present invention relates to a diagnostic kit which comprises:

(a) a polynucleotide of the present invention, preferably the nucleotide sequence of SEQ ID NO:1,3,5,7 or a fragment thereof;

(b) a nucleotide sequence complementary to that of (a);

(c) a polypeptide of the present invention, preferably the polypeptide of SEQ ID NO:2,4,6,8 or a fragment thereof; or (d) an antibody to a polypeptide of the present invention, preferably to the polypeptide of SEQ ID NO:2,4,6,8.

It will be appreciated that in any such kit, (a), (b), (c) or (d) may comprise a substantial component. Such a kit will be of use in diagnosing a disease or susceptibility to a disease, among others.

This invention also relates to the use of polynucleotides of the present invention as diagnostic reagents. Detection of a mutated form of a polynucleotide of the invention, preferably of SEQ ID NO:1,3,5 or 7 which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose. PCR. As an example, PCR primers complementary to a polynucleotide encoding BASB047, BASB054, BASB068 or BASB069 polypeptide can be used to identify and analyze mutations.

The invention further provides primers with 1, 2, 3 or 4 nucleotides removed from the 5' and/or the 3' end. These primers may be used for, among other things, amplifying BASB047, BASB054, BASB068 or BASB069 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing disease, preferably bacterial infections, more preferably infections caused by *Neisseria meningitidis*, comprising determining from a sample derived from an individual, such as a bodily material, an increased level of expression of polynucleotide having a sequence of SEQ ID NO:1,3,5 or 7. Increased or decreased expression of a BASB047, BASB054, BASB068 or BASB069 polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB047, BASB054, BASB068 or BASB069 polypeptide compared to normal control tissue samples may be used to detect the presence of an infection, for example. Assay techniques that can be used to determine levels of a BASB047, BASB054, BASB068 or BASB069 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probe obtained or derived from a bodily sample, to determine the presence of a particular polynucleotide sequence or related sequence in an individual. Such a presence may indicate the presence of a pathogen, particularly *Neisseria meningitidis*, and may be useful in diagnosing and/or prognosing disease or a course of disease. A grid comprising a number of variants of the polynucleotide sequence of SEQ ID NO:1, 3,5,7 are preferred. Also preferred is a grid comprising a number of variants of a polynucleotide sequence encoding the polypeptide sequence of SEQ ID NO:2,4,6 or 8.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against BASB047, BASB054, BASB068 or BASB069 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB047, BASB054, BASB068 or BASB069 or from naive libraries (McCafferty, et al., (1990), *Nature* 348, 552–554; Marks, et al., (1992) *Biotechnology* 10, 779–783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB047, BASB054, BASB068 or BASB069-polypeptide or BASB047, BASB054, BASB068 or BASB069-polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al., (1986), *Nature* 321, 522–525 or Tempest et al., (1991) *Biotechnology* 9, 266–273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB047, BASB054, BASB068 or BASB069 polypeptide and/or polynucleotide activity in the mixture, and comparing the BASB047, BASB054, BASB068 or BASB069 polypeptide and/or polynucleotide activity of the mixture to a standard. Fusion proteins, such as those made from Fc portion and BASB047, BASB054, BASB068 or BASB069 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., *J Biol Chem*, 270(16):9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB047, BASB054, BASB068 or BASB069 polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB047, BASB054, BASB068 or BASB069 polypeptide and a labeled substrate or ligand of such polypeptide is incubated in the absence or the presence of a candidate molecule that may be a BASB047, BASB054, BASB068 or BASB069 agonist or antagonist. The ability of the candidate molecule to agonize or antagonize the BASB047, BASB054, BASB068 or BASB069 polypeptide is reflected in decreased binding of the labeled ligand or decreased production of product from such substrate. Molecules that bind gratuitously, i.e., without inducing the effects of BASB047, BASB054, BASB068 or BASB069 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in BASB047, BASB054, BASB068 or BASB069 polynucleotide or polypeptide activity, and binding assays known in the art.

Another example of an assay for BASB047, BASB054, BASB068 or BASB069 agonists is a competitive assay that combines BASB047, BASB054, BASB068 or BASB069 and a potential agonist with BASB047, BASB054, BASB068 or BASB069-binding molecules, recombinant BASB047, BASB054, BASB068 or BASB069 binding molecules, natural substrates or ligands, or substrate or ligand mimetics, under appropriate conditions for a competitive inhibition assay. BASB047, BASB054, BASB068 or BASB069 can be labeled, such as by radioactivity or a calorimetric compound, such that the number of BASB047, BASB054, BASB068 or BASB069 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB047, BASB054, BASB068 or BASB069-induced activities, thereby preventing the action or expression of BASB047, BASB054, BASB068 or BASB069 polypeptides and/or polynucleotides by excluding BASB047, BASB054, BASB068 or BASB069 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of BASB047, BASB054, BASB068 or BASB069.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor $X_a$. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB047, BASB054, BASB068 or BASB069 proteins that mediate tissue damage and/or; to block the normal progression of pathogenesis in infections initiated other than by the implantation of in-dwelling devices or by other surgical techniques.

In accordance with yet another aspect of the invention, there are provided BASB047, BASB054, BASB068 or BASB069 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB047, BASB054, BASB068 or BASB069 polynucleotide and/or polypeptide, or a fragment or variant thereof, adequate to produce antibody and/or T cell immune response to protect said individual from infection, particularly bacterial infection and most particularly *Neisseria meningitidis* infection. Also provided are methods whereby such immunological response slows bacteria replication. Yet another aspect of the invention relates to a method of inducing immunological response in an individual which comprises delivering to such individual a nucleic acid vector, sequence or ribozyme to direct expression of BASB047, BASB054, BASB068 or BASB069 polynucleotide and/or polypeptide, or a fragment or a variant thereof, for expressing BASB047, BASB054, BASB068 or BASB069 polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB047, BASB054, BASB068 or BASB069 polynucleotide and/or polypeptide encoded therefrom, wherein the composition comprises a recombinant BASB047, BASB054, BASB068 or BASB069 polynucleotide and/or polypeptide encoded therefrom and/or comprises DNA and/or RNA which encodes and expresses an antigen of said BASB047, BASB054, BASB068 or BASB069 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+T cells.

A BASB047, BASB054, BASB068 or BASB069 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

In a vaccine composition according to the invention, a BASB047, BASB054, BASB068 or BASB069 polypeptide and/or polynucleotide, or a fragment, or a mimotope, or a variant thereof may be present in a vector, such as the live recombinant vectors described above for example live bacterial vectors.

Also suitable are non-live vectors for the BASB047, BASB054, BASB068 or BASB069 polypeptide, for example bacterial outer-membrane vesicles or "blebs". OM blebs are derived from the outer membrane of the two-layer membrane of Gram-negative bacteria and have been documented in many Gram-negative bacteria (Zhou, L et al. 1998. *FEMS Microbiol. Lett.* 163:223–228) including *C. trachomatis* and *C. psittaci*. A non-exhaustive list of bacterial pathogens reported to produce blebs also includes: *Bordetella pertussis, Borrelia burgdorferi, Brucella melifensis, Brucella ovis. Esherichia coli. Haemophilits influenza, Legionelia pneumophila, Neisseria gonorrhoeae, Neisseria meningitidis, Pseudomonas aeruginosa* and *Yersinia enterocolitica*.

Blebs have the advantage of providing outer-membrane proteins in their native conformation and are thus particularly useful for vaccines. Blebs can also be improved for vaccine use by engineering the bacterium so as to modify the expression of one or more molecules at the outer membrane. Thus for example the expression of a desired immunogenic protein at the outer membrane, such as the BASB047, BASB054, BASB068 or BASB069 polypeptide, can be introduced or upregulated (e.g. by altering the promoter). Instead or in addition, the expression of outer-membrane molecules which are either not relevant (e.g. unprotective antigens or immunodominant but variable proteins) or detrimental (e.g. toxic molecules such as LPS, or potential inducers of an autoimmune response) can be downregulated. These approaches are discussed in more detail below.

The non-coding flanking regions of the BASB047, BASB054, BASB068 or BASB069 gene contain regulatory elements important in the expression of the gene. This regulation takes place both at the transcriptional and translational level. The sequence of these regions, either upstream or downstream of the open reading frame of the gene, can be obtained by DNA sequencing. This sequence information allows the determination of potential regulatory motifs such as the different promoter elements, terminator sequences, inducible sequence elements, repressors, elements responsible for phase variation, the shine-dalgarno sequence, regions with potential secondary structure involved in regulation, as well as other types of regulatory motifs or sequences.

This sequence information allows the modulation of the natural expression of the BASB047, BASB054, BASB068 or BASB069 gene. The upregulation of the gene expression may be accomplished by altering the promoter, the shine-dalgarno sequence, potential repressor or operator elements, or any other elements involved. Likewise, downregulation of expression can be achieved by similar types of modification.

Alternatively, by changing phase variation sequences, the expression of the gene can be put under phase variation control, or it may be uncoupled from this regulation. In another approach, the expression of the gene can be put under the control of one or more inducible elements allowing regulated expression. Examples of such regulation include, but are not limited to, induction by temperature shift, addition of inductor substrates like selected carbohydrates or their derivatives, trace elements, vitamins, co-factors, metal ions, etc.

Such modifications as described above can be introduced by several different means. The modification of sequences involved in gene expression can be carried out in vivo by random mutagenesis followed by selection for the desired phenotype. Another approach consists in isolating the region of interest and modifying it by random mutagenesis, or site-directed replacement, insertion or deletion mutagenesis. The modified region can then be reintroduced into the bacterial genome by homologous recombination, and the effect on gene expression can be assessed; In another approach, the sequence knowledge of the region of interest can be used to replace or delete all or part of the natural regulatory sequences. In this case, the regulatory region targeted is isolated and modified so as to contain the regulatory elements from another gene, a combination of regulatory elements from different genes, a synthetic regulatory region, or any other regulatory region, or to delete selected parts of the wild-type regulatory sequences. These modified sequences can then be reintroduced into the bacterium via homologous recombination into the genome. A non-exhaustive list of preferred promoters that could be used for up-regulation of gene expression includes the promoters porA, porB, lbpB, tbpB, p110, lst, hpuAB from *N. meningitidis* or *N. gonorroheae*; ompCD, copB, lbpB, ompE, UspA1; UspA2; TbpB from *M. Catarrhalis*; p1, p2, p4, p5, p6, lpD, tbpB, D15, Hia, Hmw1, Hmw2 from *H. influenzae*.

In one example, the expression of the gene can be modulated by exchanging its promoter with a stronger promoter (through isolating the upstream sequence of the gene, in vitro modification of this sequence, and reintroduction into the genome by homologous recombination). Upregulated expression can be obtained in both the bacterium as well as in the outer membrane vesicles shed (or made) from the bacterium.

In other examples, the described approaches can be used to generate recombinant bacterial strains with improved characteristics for vaccine applications. These can be, but are not limited to, attenuated strains, strains with increased expression of selected antigens, strains with knock-outs (or decreased expression) of genes interfering with the immune response, strains with modulated expression of immunodominant proteins, strains with modulated shedding of outer-membrane vesicles.

Thus, also provided by the invention is a modified upstream region of the BASB047, BASB054, BASB068 or BASB069 gene, which modified upstream region contains a heterologous regulatory element which alters the expression level of the BASB047, BASB054, BASB068 or BASB069 protein located at the outer membrane. The upstream region according to this aspect of the invention includes the sequence upstream of the BASB047, BASB054, BASB068 or BASB069 gene. The upstream region starts immediately upstream of the BASB047, BASB054, BASB068 or BASB069 gene and continues usually to a position no more than about 1000 bp upstream of the gene from the ATG start codon. In the case of a gene located in a polycistronic sequence (operon) the upstream region can start immediately preceding the gene of interest, or preceding the first gene in the operon. Preferably, a modified upstream region according to this aspect of the invention contains a heterologous promotor at a position between 500 and 700 bp upstream of the ATG.

Thus, the invention provides a BASB047, BASB054, BASB068 and BASB069 polypeptide, in a modified bacterial bleb. The invention further provides modified host cells capable of producing the non-live membrane-based bleb vectors. The invention further provides nucleic acid vectors comprising the BASB047, BASB054, BASB068 and BASB069 gene having a modified upstream region containing a heterologous regulatory element.

Further provided by the invention are processes to prepare the host cells and bacterial blebs according to the invention.

Also provided by this invention are compositions, particularly vaccine compositions, and methods comprising the polypeptides and/or polynucleotides of the invention and immunostimulatory DNA sequences, such as those described in Sato, Y. et al. *Science* 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Neisseria meningitidis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Neisseria meningitidis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (AMosmann, T. R. and Coffman, R. L. (1989) *TH*1 and TH2 cells: different patterns of lymphokine secretion lead to different functional properties. Annual Review of Immunology, 7, p145–173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a T1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454). 3D-MPL will be present in the range of 10 $\mu$g–100 $\mu$g preferably 25–50 $\mu$g per dose wherein the antigen will typically be present in a range 2–50 $\mu$g per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with a carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing, an adjuvant which is a preferential stimulator of TH1 cell response. For example, QS21 can be formulated together with 3D-MPL. The ratio of QS21: 3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 $\mu$g–200 $\mu$g, such as 10–100 $\mu$g, preferably 10 $\mu$g–50 $\mu$g per dose. Typically the oil in water will comprise from 2 to 10% squalene, from 2 to 10% alpha tocopherol and from 0.3 to 3% tween 80. Preferably the ratio of squalene:alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB047, BASB054, BASB068 and BASB069 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

The antigen can also be delivered in the form of whole bacteria (dead or alive) or as subcellular fractions, these possibilities do include *N.meningitidis* itself.

Compositions, Kits and Administration

In a further aspect of the invention there are provided compositions comprising a BASB047, BASB054, BASB068 or BASB069 polynucleotide and/or a BASB047, BASB054, BASB068 or BASB069 polypeptide for administration to a cell or to a multicellular organism.

The invention also relates to compositions comprising a polynucleotide and/or a polypeptide discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1–100 μg/kg of subject.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Definitions

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York. 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press. 1987: and *Sequence Analysis Primer*, Gribskov, M. and Devereux, J., eds., M Stockton Press, New York, 1991; and Carillo, H., and Lipman, D., SIAM J. *Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J Mol. Biol* 215: 403–410 (1990), and FASTA(Pearson and Lipman *Proc. Natl. Acad. Sci. USA* 85; 2444–2448 (1988). The BLAST family of programs is publicly available from NCRI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:

Algorithm: Needleman and Wunsch, *J. Mol Biol.* 48: 443–453 (1970)

Comparison matrix: BLOSSUM62 from Henikoff and Henikoff,

Proc. Natl. Acad. Sci. USA. 89:10915–10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, *J. Mol Biol.* 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \circ Y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and $\circ$ is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \circ y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., $\circ$ is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \circ y)$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and $\circ$ is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \circ y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and $\circ$ is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, upper respiratory tract infection, invasive bacterial diseases, such as bacteremia and meningitis.

EXAMPLES

The examples below are carried out using standard techniques, which are well known and routine to those of skill in the art, except where otherwise described in detail. The examples are illustrative, but do not limit the invention.

Example 1

The BASB047 Gene in *N.meningitidis* Strain ATCC 13090

The BASB047 gene of *N. meningitidis* strain ATCC 13090 is shown in SEQ ID NO:1. The translation of the BASB047 polynucleotide sequence, shown in SEQ ID NO:2, shows significant similarity to *E. coli* ferric aerobactin receptor precursor (cloacin receptor). The BASB047 polypeptide contains a sequence which has the characteristics of a leader signal sequence. The signal sequence would be cleaved after residue 25 of the sequence shown in SEQ ID NO:2. BASB047 has the characteristics of an outer membrane protein involved iron uptake.

Example 2

The BASB054 Gene in *N.meningitidis* Strain ATCC13090

The BASB054 gene of *N. meningitidis* strain ATCC 13090 is shown in SEQ ID NO:3. The translation of the BASB054 polynucleotide sequence, shown in SEQ ID NO:4, shows significant similarity to a *E. coli* organic solvent tolerance protein. The BASB054 polypeptide contains a sequence which has the characteristics of a leader signal sequence. This signal sequence would be cleaved after residue 22 of the SEQ ID NO:4 polypeptide.

Example 3

The BASB068 Gene in *N.meningitidis* Strain ATCC13090

The BASB068 gene of *N. meningitidis* strain ATCC 13090 is shown in SEQ ID NO:5. The translation of the BASB068 polynucleotide sequence, shown in SEQ ID NO:6, shows significant similarity to *E. coli* AIDA-I protein. The BASB068 polypeptide contains a sequence which has the characteristics of a leader signal sequence. This signal sequence would be cleaved after residue 34 of the polypeptide in SEQ ID NO:6. BASB068 has the characteristics of an outer membrane protein.

Example 4

The BASB069 Gene in *N.meningitidis Strain ATCC* 13090

The BASB069 gene of *N. meningitidis* strain ATCC 13090 is shown in SEQ ID NO:7. The translation of the BASB069 polynucleotide sequence, shown in SEQ ID NO:8, shows significant similarity to *E. coli* AIDA-I protein. The BASB069 polypeptide contains a sequence which has the characteristics of a leader signal sequence. This signal sequence would be cleaved after residue 31 of the sequence of SEQ ID NO:8. BASB069 has the characteristics of an outer membrane protein.

Polynucleotide and Polypeptide Sequences

SEQ ID NO:1

*Neisseria meningitidis* BASB047 polynucleotide sequence from strain ATCC 13090

ATGCGTCATTCCCACTATTTTCAATGGTTATCTTTGCCTTTACTAAGTGTGGCAGTAACT

CAGCAGTTGTACGCTCAACCCAATGAGTCATTACCAACGGTTGAATTAGAGCCTGTGGTT

ATTACCATTGATAAGAGCGGTATGGCACTTGCCAATCGTATCACGCAAATGCCCCATACC

ACCAAAGTTATTTATGAAGAGCAAATTCAAGAGCAAGCAACAGGCTCTCGACAGCTTGCC

GATGTGATGGCACAGCTCATTCCAAGTTTGGGGGTAAGTAGTGGCACTACCAGTAACTTT

GGGCAAACCATGCACGGTCGTCAAGTGCAATTTTTGTTAAATGGCGTGCCTTTGACAGGT

TCGCGAGACATCTCTAGACAGCTTAATAGTATCAATCCCAATCAAGTGGCTAGAATTGAA

GTTTTATCAGGAGCAACCAGTATTTATGGGTCTGGAGCAACAGGCGGTTTGATTAATATC

GTTACTAAGTCTGATTTGGAAGAGGAGCAATTTGAAACCCGCATCGGTGTACATGGTAGT

AAATTATCCAGTGAAGGTATCGGTTATCAGGTAGGTCAGAGTGTAGCAGGTGTCAGCGAA

AATGGTAATGTCCTTGCACGACTTGATGTCGACTATCGCACCACAGGAGGGGCATTTGAT

GCTAACGGTAAACGCATCGCTCCTGAGCCTGCCCAAACTGATAAGCAAGACAGCAAAAGC

CTAAGTGTCAATACAAATGTTGATTGGCAACTTGACGACAAGCAAAATATCAATCTGGCA

TTGACGCATTATAACGACAAACAAGATACCGATTATGCACCTGATTATGGTAATCGCCTT

GCGGTGTTGTTTGGAGAAAAGCCTTCATTAAATGCCATCAAAGGCTTATCATTATCAGAA

CAGCCAAAAACCACCAAAAGCACCTTTAATATCAACTATCATCATGATGATTTGTGGGGT

AACACCATCAATACCAATGCTTATTATCGCAGAGAGAAAGGCAGATTTTATCCCTTTGTT

GCCCCGTTTTCGATCGCCAAAGCCCTGCCTATTTTACAAAGCATGAATTTGCCATCAGCC

ACTTTGGATGCTTATACCAAGGCTCCACAAGCTCGCGCCTATGGGGTGTTACAATCCGAA

TCTAAGGCAGAGGTACTAGGGCGTGTCCCTAATTTGAATAAGCCCAAAAGAGCCCTATTT

TAA

SEQ ID NO:2

*Neisseria meningitidis* BASB047 polypeptide sequence deduced from the polynucleotide sequence of SEQ ID NO:1

MRHSHYFQWLSLPLLSVAVTQQLYAQPNESLPTVELEPVVITIDKSGMALANRITQMPHT

TKVIYEEQIQEQATGSRQLADVMAQLIPSLGVSSGTTSNFGQTMHGRQVQFLLNGVPLTG

SRDISRQLNSINPNQVARIEVLSGATSIYGSGATGGLINIVTKSDLEEEQFETRIGVHGS

KLSSEGIGYQVGQSVAGVSENGNVLARLDVDYRTTGGAFDANGKRIAPEPAQTDKQDSKS

LSVNTNVDWQLDDKQNINLALTHYNDKQDTDYAPDYGNRLAVLFGEKPSLNAIKGLSLSE

QPKTTKSTFNINYHHDDLWGNTINTNAYYRREKGRFYPFVAPFSIAKALPILQSMNLPSA

TLDAYTKAPQARAYGVLQSESKAEVLGRVPNLNKPKRALF

SEQ ID NO:3

*Neisseria meningitidis* BASB054 polynucleotide sequence from strain ATCC 13090

TTGGCTCGTTTATTTTCACTCAAACCACTGGTGCTGGCATTGGGCTTCTGCTTCGGCACG

CATTGCGCCGCCGCCGATGCCGTTGCGGCGGAGGAAACGGACAATCCGACCGCCGGAGGA

AGTGTTCGGAGCGTGTCCGAACCCATGCAGCCTGCCGGCCTGAGCCTCGGTTCGACCTGC

CTGTTTTGCAGTAACGAAAGCGGCAAACCCGAAAAAAACCGAATCTGCCGTCAAAGGAAGC

-continued

```
GGCGAAGGGCCTGTGCCCGAAAACCACACGCGAATTGTCGCCGACAAGGTGGAAGGGCAG

TCGCAGGTCAAGGTACGCGCGGAGGGCGGCGTCGTTGTCGAACGCAACCGGACGACCCTT

AATGCCGACTGGGCGGATTACGACCAGTCGGGCGACACCGTTACCGTAGGCGACCGGTTC

GCCCTCCAACAGGACGGTACGCTGATTCGGGGCGAAACCCTGACCTACAATCTCGAGCAG

CAGACCGGCGAAGCGCACAACGTCCGCATGGAAACCGAACAAGGCGGACGGCGGCTGCAA

AGCGTCAGCCGCACCGCCGAAATGTTGGGCGAAGGGCATTACAAACTGACGGAAACCCAA

TTCAACACCTGTTCCGCCGGCGATGCCGGCTGGTATGTCAAGGCAGCCTCTGTCGAAGCC

GATCGGGAAAAAGGCATAGGCGTTGCCAAACACGCCGCCTTCGTGTTCGGCGGCGTTCCT

ATTTTCTACACCCCTTGGGCGGACTTCCCGCTTGACGGCAACCGCAAAAGCGGCCTGCTT

GTTCCCTCACTGTCCGCCGGTTCGGACGGCGTTTCCCTTTCCGTTCCCTATTATTTCAAC

CTTGCCCCCAATCTCGATGCCACGTTCGCGCCCAGCGTGATCGGCGAACGCGGCGCGGTC

TTTGACGGGCAGGTACGCTACCTGCGGCCGGATTATGCCGGCCAGTCCGACCTGACCTGG

CTGCCGCACGACAAGAAAAGCGGCAGGAATAACCGCTATCAGGCGAAATGGCAGCATCGG

CACGACATTTCCGACACGCTTCAGGCGGGTGTCGATTTCAACCAAGTCTCCGACAGCGGC

TACTACCGCGACTTTTACGGCAACAAAGAAATCGCCGGCAACGTCAACCTCAACCGCCGT

GTATGGCTGGATTATGGCGGCAGGGCGGCGGGCGGCAGCCTGAATGCCGGCCTTTCGGTT

CTGAAATACCAGACGCTGGCAAACCAAAGCGGCTACAAAGACAAACCGTATGCCCTGATG

CCGCGCCTTTCCGCCGATTGGCGCAAAAACACCGGCAGGGCGCAAATCGGCGTGTCCGCA

CAATTTACCCGCTTCAGCCACGACAGCCGCCAAGACGGCAGCCGCCTCGTCGTCTATCCC

GACATCAAATGGGATTTCAGCAACAGCTGGGGTTACGTCCGTCCCAAACTCGGACTGCAC

GCCACCTATTACAGCCTCAACCGCTTCGGCAGCCAAGAAGCCCGACGCGTCAGCCGCACT

CTACCCATCGTCAACATCGACAGCGGCATGACCTTCGAACGCAATACGCGGATGTTCGGC

GGAGAAGTCCTGCAAACCCTCGAGCCGCGCCTGTTCTACAACTATATTCCTGCCAAATCC

CAAAACGACCTGCCCAATTTTGATTCGTCGGAAAGCAGCTTCGGCTACGGGCAGCTTTTT

CGTGAAAACCTCTATTACGGCAACGACAGGATTAACACCGCAAACAGCCTTTCCGCCGCC

GTGCAAAGCCGTATTTTGGACGGCGCGACGGGGCAGAGCGTTTCCGCGCCGGCATCGGG

CAGAAATTCTACTTCAAAAACGACGCAGTCATGCTTGACGGCAGTGTCGGCAAAAAACCG

CGCAGCCGTTCCGACTGGGTGGCATTCGCCTCCAGCGGCATCGGCAGCCGCCTTCATCCTC

GACAGCAGCATCCACTACAACCAAAACGACAAACGCGCCGAGAACTACGCCGTCGGTGCA

AGCTACCGTCCCGCACAGGGCAAAGTGCTGAACGCCCGCTACAAATACGGGCGCAACGAA

AAAATCTACCTGAAGTCCGACGGTTCCTATTTTTACGACAAACTCAGCCAGCTCGACCTG

TCCGCACAATGGCCCCTGACGCGCAACCTGTCGGCCGTCGTCCGTTACAACTACGGTTTT

GAAGCCAAAAAACCGATAGAGGTGCTGGCGGGTGCGGAATACAAAAGCAGTTGCGGCTGC

TGGGGCGCGGGCGTGTACGCCCAACGCTACGTTACCGGCGAAAACACCTACAAAAACGCT

GTCTTTTTCTCACTTCAGTTGAAAGACCTCAGCAGTGTCGGCAGAAACCCCGCAGACAGG

ATGGATGTCGCCGTTCCCGGCTATATCCCCGCCCACTCTCTTTCCGCCGGACGCAACAAA

CGGCCCTGA
```

SEQ ID NO:4

*Neisseria meningitidis* BASB054 polypeptide sequence deduced from the polynucleotide sequence of SEQ ID NO:3

MARLFSLKPLVLALGFCFGTHCAAADAVAAEETDNPTAGGSVRSVSEPMQPAGLSLGSTC

LFCSNESGKPEKTESAVKGSGEGPVPENHTRIVADKVEGQSQVKVRAEGGVVVERNRTTL

NADWADYDQSGDTVTVGDRFALQQDGTLIRGETLTYNLEQQTGEAHNVRMETEQGGRRLQ

SVSRTAEMLGEGHYKLTETQFNTCSAGDAGWYVKAASVEADREKGIGVAKHAAFVFGGVP

IFYTPWADFPLDGNRKSGLLVPSLSAGSDGVSLSVPYYFNLAPNLDATFAPSVIGERGAV

FDGQVRYLRPDYAGQSDLTWLPHDKKSGRNNRYQAKWQHRHDISDTLQAGVDFNQVSDSG

YYRDFYGNKEIAGNVNLNRRVWLDYGGRAAGGSLNAGLSVLKYQTLANQSGYKDKPYALM

PRLSADWRKNTGRAQIGVSAQFTRFSHDSRQDGSRLVVYPDIKWDFSNSWGYVRPKLGLH

ATYYSLNRFGSQEARRVSRTLPIVNIDSGMTFERNTRMFGGEVLQTLEPRLFYNYIPAKS

QNDLPNFDSSESSFGYGQLFRENLYYGNDRINTANSLSAAVQSRILDGATGAERFRAGIG

QKFYFKNDAVMLDGSVGKKPRSRSDWVAFASSGIGSRFILDSSIHYNQNDKRAENYAVGA

SYRPAQGKVLNARYKYGRNEKIYLKSDGSYFYDKLSQLDLSAQWPLTRNLSAVVRYNYGF

EAKKPIEVLAGAEYKSSCGCWGAGVYAQRYVTGENTYKNAVFFSLQLKDLSSVGRNPADR

MDVAVPGYIPAHSLSAGRNKRP

SEQ ID NO:5

*Neisseria meningitidis* BASB068 polynucleotide sequence from strain ATCC 13090

ATGAAACTCGAAGCAAGCAAGCAAGCAAGCAAGCAGAAGTTTAAAAAATCATTTATTATA

AGTCTATTTTTTTCTATTCTTTATACCTCTCCGCTTTTGGCTGTTGATTACGTTTACGAC

AAAACCAAGCTCACTGATGATGAAATTACCCGCTTAAAAAAACTCCGCGATAGAAATAGT

GAATATTGGAAAGAAGAAACTTATCACATAAAAAGTAACAACCGAGTTTATCCAAACATT

CCCGCATTATTCCCTAAACATCCTTTCGATCCATTCGAAAACATCAATAATTCAAAAAGG

ATTTCTTTTTATGACAAAGAATACACTGAAGATTACCTTGTTGGTTTTGCTCAAGGTTTA

GGCGTTGCAAAAAGAAATGGGGAAACAGAAAAACCAATACGGCAATATTTTAAGGAATGT

TTAAACACTGGGAAATATAGTGATGATACTTGCAAATCTCAACAATCTATTCCTACAGTA

AGAAGTGATATTTTCGCCCTAAATACGAAAATAAAAAATAGCCATATCAACAGCGAAATT

TTCGCTGTCGGTAATTATACAAAATTGATGTACTCAGCCCAACATCATTCTATTTGGTCA

GAGCATCTCTATTCCAATTCAGAATTATCTCTTGACGTTGATAACTCACACGTTATCGGA

CAAACGATTGATTTGGGAGCATTAGAATTAACAAATTCTCTATGGGAACCCCGTTGGAAC

TCTAATATTGATTATTTAATAACAAAAAATGCTGAAATTCGTTTTAACACTAAAAGTGAA

AGTTTACTCGTAAAAGAAGATTATGCTGCCGGAGCTCGTTTTCGTTTTGCTTACGGTCTA

AAAGATAAAGTCCCTGAAACACCAATTTTAACTTTTGAAAAAAATATAACTGGCACATCA

GATATTATTTTTGAGGGAAAAGCGTTGGATAATTTAAAACACCTAGACGGGCATCAAATT

ATCAAAGTAAATGGCACAGCAGATAAACACGCATTCCGTCTTTCTGGCAAACACCAAAAG

GGAATTTATACGCTTTCTTTACAACAACGCCCAGAGGGCTTTTTTACCAAAGTGCAAGAA

CGCGATGATATTGCGATTTATGCACAACAAGCCCAAGCCGCCAATACCTTATTCGCCTTG

CGTTTAAACGACAAAAACAGCGATATTTTTGACCGCACTTTACCGCGCAAAGGCTTGTGG

TTACGTGTGATTGACGGACATTCCAGCCAATGGGTACAAGGCAAAACGGCACCAGTAGAA

-continued

GGAAATCGTAAAGGCATACAACTTGGTGGCGATGTTTTCTCATTGCAAAATCACAACTAT

CAACTTTCCGTTGGCTTAATGGGCGGACAAGCAGAACAACGCAGTACTTTCCGCAACCCA

GATACAGACAATCTTACAACGGGAAATGTGAAAGGCTTTGGTGCAGGCGTTTACGCCACT

TGGCATCAGCTTCAGGACAAACAGACAGGTGCGTATGCGGATAGCTGGGTACAATATCAA

CGTTTCCGCCACCGTATCAACACTGAAGATGGTACAGAACGTTTTACTTCAAAAGGTATT

ACTGCCTCAATTGAAGCAGGTTACAACGCTTTATTGGCGGAACACGTAACTAAAAAGGGC

AACAGCCTTCGTGTTTACCTACAACCACAGGCGCAATTGACTTATTTGGGGGTAAACGGA

AAATTCAGCGATAGCGAAAATGCCCACGTGAATTTACTTGGCTCTCGCCAATTACAAAGC

CGAGTGGGCGTTCAAGCTAAAGCTCAATTTGCTTTCACTAATGGCGTCACTTTCCAACCA

TTTGTTTCCGTCAATTCAATCTACCAACAAAAACCTTTCGGGGTAGAAATGGACGGAGAA

CGTCGAGTGATAAACAACAAAACCGCGATTGAAAGCCAATTAGGCGTTGCGGTAAAAATT

AAATCTCACTTAACTTTACAAGCAACATTCAACCGCCAAACAGGCAAACATCATCAAGCT

AAACAAGGCGCATTGAATTTACAGTGGACGTTTTAA

SEQ ID NO:6

*Neisseria meningitidis* BASB068 polypeptide sequence deduced from the polynucleotide sequence of SEQ ID NO:5

MKLEASKQASKQKFKKSFIISLFFSILYTSPLLAVDYVYDKTKLTDDEITRLKKLRDRNS

EYWKEETYHIKSNNRVYPNIPALFPKHPFDPFENINNSKRISFYDKEYTEDYLVGFAQGL

GVAKRNGETEKPIRQYFKECLNTGKYSDDTCKSQQSIPTVRSDIFALNTKIKNSHINSEI

FAVGNYTKLMYSAQHHSIWSEHLYSNSELSLDVDNSHVIGQTIDLGALELTNSLWEPRWN

SNIDYLITKNAEIRFNTKSESLLVKEDYAGGARFRFAYGLKDKVPETPILTFEKNITGTS

DIIFEGKALDNLKHLDGHQIIKVNGTADKHAFRLSGKHQKGIYTLSLQQRPEGFFTKVQE

RDDIAIYAQQAQAANTLFALRLNDKNSDIFDRTLPRKGLWLRVIDGHSSQWVQGKTAPVE

GNRKGIQLGGDVFSLQNHNYQLSVGLMGGQAEQRSTFRNPDTDNLTTGNVKGFGAGVYAT

WHQLQDKQTGAYADSWVQYQRFRHRINTEDGTERFTSKGITASIEAGYNALLAEAVTKKG

NSLRVYLQPQAQLTYLGVNGKFSDSENAHVHLLGSRQLQSRVGVQAKAQFAFTNGVTFQP

FVSVNSIYQQKPFGVEMDGERRVINNKTAIESQLGVAVKIKSHLTLQATFNRQTGKHHQA

KQGALNLQWTF

SEQ ID NO:7

*Neisseria meningitidis* BASB069 polynucleotide sequence from strain ATCC 13090

ATGACACTGAAAGCAAGCAAGCAAGCAAGCGGTCGGGTTAATCTATTAACATTATCTGTT

TTATCGCTGTTTTGCACGCCATATGTTTGTGGTTCGGATGCGTACGATCCCGTCAAAGAA

GCCGAGATTAAAAACAAATTTATTTTAGAAGCGGCGGAAGACAGAAATTCCCACGTTTGG

CGCGGCCCGTGCAGCATATCTTTTGATTGCTTCGGTATGTTCAGAGCTCAGCTTGGTTCA

AATACTCGTTCTACCAAAATCGGCGACGATGCCGATTTTTCATTTTCAGACAAGCCGAAA

CCCGGCACTTCCCATTATTTTTCCAGCGGTAAAACCGATCAAAATTCATCCGAATATGGG

TATGACGAAATCAATATCCAAGGTAAAAACTACAATAGCGGCATACTCGCCGTCGATAAT

ATGCCCGTTGTTAAGAAATATATTACAGATACTTACGGGGATAATTTAAAGGATGCGGTT

AAGAAGCAATTACAGGATTTATACAAAACAAGACCCGAAGCTTGGGAAGAAAATAAAAAA

CGGACTGAGGAGGCGTATATAGAACAGCTTGGACCAAAATTTAGTATACTCAAACAGAAA

-continued

AACCCCGATTTAATTAATAAATTGGTAGAAGATTCCGTACTCACTCCTCATAGTAATACA

TCACAGACTAGTCTCAACAACATCTTCAATAAAAAATTACACGTCAAAATCGAAAACAAA

TCCCACGTCGCCGGACAGGTGTTGGAACTGACCAAGATGACGCTGAAAGATTCCCTTTGG

GAACCGCGCCGCCATTCCGACATCCATACGCTGGAAACTTCCGATAATGCCCGCATCCGC

CTGAACACGAAAGATGAAAAACTGACCGTCCATAAAGCGTATCAGGGCGGCGCGGATTTC

CTGTTCGGCTACGACGTGCGGGAGTCGGACGAACCCGCCCTGACCTTTGAACAAAACGTC

AGCGGAAAATCCGGCGTGGTTTTGGAACGCCGGCCGGAAAATCTGAAAACGCTCGACGGG

CGCAAACTGATTGCGGCGGAAAAGGCAGACCCTAATTCGTTTGCGTTTAAACAAAATTAC

CGGCAGGGACTGTACGAATTATTGCTCAAGCAATGCGAAGGCGGATTTTGCTTGGGTGTG

CAGCGTTTGGCTATCCCTGAGGCGGAAGCGGTTTTATATGCCCAACAGGCTTATGCGGCA

AATACTTTGTTTGGGCTGCGTGCCGCCGACAGGGGCGACGACGTGTATGCCGCCGATCCG

TCCCGTCAAAAATTGTGGCTGCGCTTCATCGGCGGCCGGTCGCATCAAAATATACGGGGC

GGCGCGGCTGCGGACGGGCGGCGCAAAGGCGTGCAAATCGGCGGTGAGGTGTTTGTACGG

CAAAATGAAGGCAGTCGGCTGGCAATCGGCGTGATGGGCGGCAGGGCTGGCCAGCACGCA

TCAGTCAACGGCAAAGGCGGTGCGGCAGGCAGTTATTTGCATGGTTATGGCGGGGGTGTT

TATGCTGCGTGGCATCAGTTGCGCGATAAACAAACGGGTGCGTATTTGGACGGCTGGTTG

CAATACCAACGTTTCAAACACCGCATCAATGATGAAAACCGTGCGGAACGCTACAAAACC

AAAGGTTGGACGGCTTCTGTCGAAGGCGGCTACAACGCGCTTGTGGCGGAAGGCGTTGTC

GGAAAAGGCAATAATGTGCGGTTTTACCTGCAACCGCAGGCGCAGTTTACCTACTTGGGC

GTAAACGGCGGCTTTACCGACAGCGAGGGGACGGCGGTCGGACTGCTCGGCAGCGGTCAG

TGGCAAAGCCGCGCCGGCATTCGGGCAAAAACCCGTTTTGCTTTGCGTAACGGTGTCAAT

CTTCAGCCTTTTGCCGCTTTTAATGTTTTGCACAGGTCAAAATCTTTCGGCGTGGAAATG

GACGGCGAAAAACAGACGCTGGCAGGCAGGACGGCGCTCGAAGGGCGGTTCGGCATTGAA

GCCGGTTGGAAAGGCCATATGTCCGCACGCATCGGATACGGCAAAAGGACGGACGGCGAC

AAAGAAGCCGCATTGTCGCTCAAATGGCTGTTTTGA

SEQ ID NO:8

*Neisseria meningitidis* BASB069 polypeptide sequence deduced from the polynucleotide sequence of SEQ ID NO:7

MTLKASKQASGRVNLLTLSVLSLFCTPYVCGSDAYDPVKEAEIKNKFILEAAEDRNSHVW

RGPCSISFDCFGMFRAQLGSNTRSTKIGDDADFSFSDKPKPGTSHYFSSGKTDQNSSEYG

YDEINIQGKNYNSGILAVDNMPVVKKYITDTYGDNLKDAVKKQLQDLYKTRPEAWEENKK

RTEEAYIEQLGPKFSILKQKNPDLINKLVEDSVLTPHSNTSQTSLNNIFNKKLHVKIENK

SHVAGQVLELTKMTLKDSLWEPRRHSDIHTLETSDNARIRLNTKDEKLTVHKAYQGGADF

LFGYDVRESDEPALTFEQNVSGKSGVVLERRPENLKTLDGRKLIAAEKADPNSFAFKQNY

RQGLYELLLKQCEGGFCLGVQRLAIPEAEAVLYAQQAYAANTLFGLRAADRGDDVYAADP

SRQKLWLRFIGGRSHQNIRGGAAADGRRKGVQIGGEVFVRQNEGSRLAIGVMGGRAGQHA

SVNGKGGAAGSYLHGYGGGVYAAWHQLRDKQTGAYLDGWLQYQRFKHRINDENRAERYKT

KGWTASVEGGYNALVAEGVVGKGNNVRFYLQPQAQFTYLGVNGGFTDSEGTAVGLLGSGQ

WQSRAGIRAKTRFALRNGVNLQPFAAFNVLHRSKSFGVEMDGEKQTLAGRTALEGRFGIE

AGWKGHMSARIGYGKRTDGDKEAALSLKWLF

Deposited Materials

A deposit containing a *Neisseria meningitidis* Serogroup B strain has been deposited with the American Type Culture Collection (herein "ATCC") on Jun. 22, 1997 and assigned deposit number 13090. The deposit was described as *Neisseria meningitidis* (Albrecht and Ghon) and is a freeze-dried, 1.5–2.9 kb insert library constructed from *N. meningitidis* isolate. The deposit is described in Int. Bull. Bacteriol. Nomenci. Taxon. 8: 1–15 (1958).

The *Neisseria meningitidis* strain deposit is referred to herein as "the deposited strain" or as "the DNA of the deposited strain."

The deposited strain contains the full length BASB047, BASB054, BASB068 and BASB069 genes. The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Microorganisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

What is claimed is:

1. An isolated, recombinant polypeptide comprising a member selected from the group consisting of
   (a) the amino acid sequence SEQ ID NO:2;
   (b) an immunogenic fragment of at least 15 contiguous amino acids of SEQ ID NO:2;
wherein the immunogenic fragment, when administered to a subject in a suitable composition which can include an adjuvant, or a suitable carrier coupled to the polypeptide, induces an antibody or T-cell mediated immune response that recognizes the polypeptide SEQ ID NO:2.

2. The isolated, recombinant polypeptide of claim 1, wherein the polypeptide is according to (a).

3. The isolated, recombinant polypeptide of claim 1, wherein the polypeptide is according to (b).

4. The isolated, recombinant polypeptide of claim 1, wherein the immunogenic fragment of (b) comprises at least 20 contiguous amino acids of SEQ ID NO:2, wherein the immunogenic fragment, when administered to a subject in a suitable composition which can include an adjuvant, or a suitable carrier coupled to the polypeptide, induces an antibody or T-cell mediated immune response that recognizes the polypeptide SEQ ID NO:2.

5. The isolated recombinant polypeptide of claim 1 wherein the isolated polypeptide of (a) consists of SEQ ID NO:2.

6. A fusion protein comprising the isolated, recombinant polypeptide of claim 1.

7. An immunogenic composition comprising the isolated, recombinant polypeptide of claim 1 and a pharmaceutically acceptable carrier.

8. The immunogenic composition of claim 7, wherein the immunogenic composition comprises at least one other *Neisseria meningitidis* antigen in addition to an antigen provided by the polypeptide.

9. A method for inducing an immune response in a mammal comprising administration of the polypeptide of claim 1.

10. An isolated polypeptide consisting of the amino acid sequence SEQ ID NO:2.

* * * * *